United States Patent [19]

Magnusson et al.

[11] Patent Number: 5,637,569
[45] Date of Patent: Jun. 10, 1997

[54] GANGLIOSIDE ANALOGS

[75] Inventors: Hans G. Magnusson; Asim K. Ray, both of Lund, Sweden

[73] Assignee: Symbicom Aktiebolag, Umea, Sweden

[21] Appl. No.: 232,240

[22] PCT Filed: Nov. 11, 1992

[86] PCT No.: PCT/DK92/00333

§ 371 Date: Sep. 12, 1994

§ 102(e) Date: Sep. 12, 1994

[87] PCT Pub. No.: WO93/10134

PCT Pub. Date: May 27, 1993

[30] Foreign Application Priority Data

Nov. 11, 1991 [DK] Denmark .................. 1853/91
Jul. 3, 1992 [DK] Denmark .................. 0880/92

[51] Int. Cl.$^6$ ............................. A61K 31/70; C07H 15/10
[52] U.S. Cl. ............................ 514/25; 536/4.1; 536/17.2; 536/17.9; 536/18.7; 536/55.2; 536/55.3
[58] Field of Search ................................. 536/4.1, 18.7, 536/53, 55.2, 53.3, 17.2, 17.9; 574/25

[56] References Cited

FOREIGN PATENT DOCUMENTS

| | | |
|---|---|---|
| 0167449 | 1/1986 | European Pat. Off. . |
| 0315113 | 5/1989 | European Pat. Off. . |
| 0319253 | 6/1989 | European Pat. Off. . |

OTHER PUBLICATIONS

Nores et al., *Density–Dependent Recognition of Cell Surface $GM_3$ by a Certain Anti–Melanoma Anti–Melanoma Antibody, and $GM_3$ Lactone as a Possible Immunogen; Requirements for Tumor–Associated Antigen and Immunogen*, The Journal of Immunology, vol. 139, No. 9, pgs. 3171–3176, Nov. 1, 1987.

Ray et al., *Synthesis nad conformational Analysis of $GM_3$Lactam, a Hydrolytically Stable Analogue of $GM_3$ Ganglioside Lactone*, J. AM. Chem. Soc., vol. 114, pp. 2256–2257, 1992.

Primary Examiner—Elli Peselev
Attorney, Agent, or Firm—Iver P. Cooper

[57] ABSTRACT

Ganglioside lactam analogue derivatives of general formula (I) in which A is a sialic acid residue of formula (II) which is bound via the dashed line in the 2-position; and in which $Z^1$ is —OH or a group —NHX$^1$, and $Y^{30}$ is —CH$_3$ or —CH$_2$OH; $X^1$ and $Y^1$ together form a bond and $Y^2$ is —OH or a group OR$^{20}$, or $X^1$ and $Y^2$ together form a bond and $Y^1$ is —OH or —NHAc; $Y^3$ is —OH or a group —OR$^{20}$; $R^1$ is H or a sialic acid residue of formula (III) which is bound via the dashed line in the 2-position; and in which $Z^2$ is —OH or a group —NHX$^2$, and $Y^{30}$ is as defined above; $X^2$ and $Y^{10}$ together form a bond and $Y^{20}$ is —OH, or $X^2$ and $Y^{20}$ together form a bond and $Y^{10}$ is —OH; with the provisos that when $R^1$ is H, then $Z^1$ is —NHX$^1$, and that when $R^1$ is a sialic acid residue of formula (III), then at least one of $Z^1$ and $Z^2$ is different from —OH; $R^{10}$ is H, a carrier CA, or a group -(Sugar)$_n$. The compounds are hydrolytically stable lactam analogs which spatially closely resemble the naturally occurring ganglioside lactones and are antigenic and able to induce the production of antibodies that cross-react with the corresponding ganglioside lactone.

7 Claims, 7 Drawing Sheets

GANGLIOSIDE ANALOGS

FIELD OF THE INVENTION

The present invention relates to analogs of gangliosides, a method for preparation of such compounds, use of such compounds to induce immune response and as inhibitors of adhesion of bacteria and viruses, as well as in the production of antibodies against the compounds, antibodies against the compounds as well as use of the antibodies in therapy or diagnosis.

BACKGROUND OF THE INVENTION

Gangliosides, i.e. sialic acid-containing glycosphingolipids, are well-known components of the mammalian cell surfaces. Furthermore, gangliosides have been found to occur in equilibrium with the corresponding lactones. Thus, $GM_3$- and $GD_3$-ganglioside [NeuAcα(2–3)Galβ(1–4)GlcβO-Ceramide and NeuAcα(2–8)NeuAcα(2–3)Galβ(1–4)GlcβO-Ceramide] have been demonstrated to form lactones where the sialic acid-derived carbonyl group enters into lactone formation with various hydroxyl groups of the NeuAc and Gal residues. Furthermore, it has been shown that such lactones exist in vivo, e.g. in brain tissue and in the membranes of tumour cells, and are not just artifacts of the isolation procedures (Gross, S. K.; Williams, M. A.; McCluer, R. H. *J. Neurochem.* 1980, 34, 1351–1361). It has also been shown that $GM_3$-lactone is much more immunogenic than is the open form of $GM_3$-ganglioside (Nores, G. A.; Dohi, T.; Taniguchi, M.; Hakomori, S.-I. *J. Immun.* 1987, 139, 3171–3176).

It has also been suggested that $GM_3$-lactone is a highly rigid structure with the lactone ring in a chair-like conformation (see scheme 1 below) which would mean that its ability to serve as a recognition site or membrane antigen could be enhanced, compared to its parent structure, which is flexible (Yu, R. K.; Koerner, T. A. W.; Ando, S.; Yohe, H. C.; Prestegaard, J. H. *J. Biochem.* 1985, 98, 1367–1373). Furthermore, the lactone of $GM_3$-ganglioside ("$GM_3$-lactone") has been suggested to be a tumour-associated antigen on the cells of an experimental mouse melanoma (Nores, G. et al. cited above). In a comparative immunization with $GM_3$-ganglioside and the corresponding lactone, the same authors showed that the lactone is the stronger immunogen, and it was suggested that this compound could be the real immunogen despite being a minor membrane component. Furthermore, the activity of a monoclonal anti-melanoma antibody (M2590) with various cells and liposomes was shown to depend in a threshold, all-or-none, fashion on the concentration of $GM_3$-ganglioside in the cell membrane or liposome. Also, the antibody was found to cross-react with $GM_3$-lactone.

The ganglioside lactones are unstable at neutral pH while acidic conditions favour the lactone in the equilibrium between $GM_3$-ganglioside and $GM_3$-lactone. However, since $GM_3$-ganglioside is itself acidic since it is an acid-containing glycolipid, the ganglioside might possibly induce its own lactonization when the concentration is sufficiently high in a cell membrane or liposome. This might help to explain the threshold effect described above and might have similar implications for other sialic acid-containing saccharides.

Thus, although a ganglioside lactone has been shown to be far more immunogenic than the open-form ganglioside, the low equilibrium concentration of the lactone at pH-values close to neutral will probably render the lactone to be a rather inefficient immunogen. Thus, it is clear that it would be desirable to have a non-labile immunogenic compound resembling the lactone form of a ganglioside and which is capable of raising antibodies (and other entities of the immune system) capable of at least partial cross-reaction with the ganglioside lactone.

SUMMARY OF THE INVENTION

In one aspect, the present invention relates to ganglioside analogs which spatially closely resemble gangliosides and which are therefore contemplated to be able to induce the production of antibodies that will cross-react with the corresponding ganglioside and in turn elicit an immune response directed against the gangliosides and thereby against entities on which the gangliosides are present.

The invention therefore relates to ganglioside lactam analogue derivatives of the general formula I

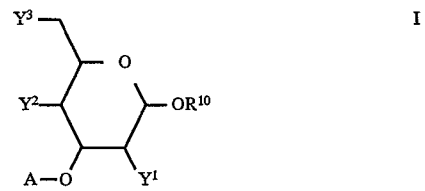

in which A is a sialic acid residue of the formula II

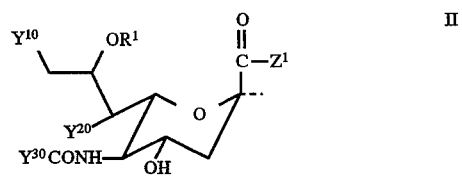

which is bound via the dashed line in the 2-position; and in which $Z^1$ is —OH or a group —$NHX^1$, and $Y^{30}$ is —$CH_3$ or —$CH_2OH$;

$X^1$ and $Y^1$ together form a bond and $Y^2$ is —OH or a group $OR^{20}$, or $X^1$ and $Y^2$ together form a bond and $Y^1$ is —OH or —NHAc;

$Y^3$ is —OH or a group —$OR^{20}$;

$R^1$ is H or a sialic acid residue of the formula III

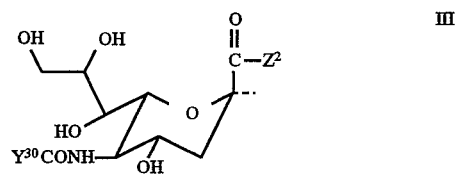

which is bound via the dashed line in the 2-position; and in which $Z^2$ is —OH or a group —$NHX^2$, and $Y^{30}$ is as defined above;

$X^2$ and $Y^{10}$ together form a bond and $Y^{20}$ is —OH, or $X^2$ and $Y^{20}$ together form a bond and $Y^{10}$ is —OH; with the provisos that when $R^1$ is H, then $Z^1$ is —$NHX^1$, and that when $R^1$ is a sialic acid residue of formula III above, then at least one of $Z^1$ and $Z^2$ is different from —OH; $R^{10}$ is H, a carrier CA, or a group -(Sugar)$_n$, in which Sugar is a monosaccharide unit selected from the group consisting of D-glucose, D-galactose, D-mannose, D-xylose, D-ribose, D-arabinose, L-fucose, 2-acetamido-2-deoxy-D-glucose, 2-acetamido-2-deoxy-D-galactose, D-glucuronic acid, D-galacturonic acid, D-mannuronic acid, 2-deoxy-2- phthalimido-D-glucose, 2-deoxy-2-phthalimido-D-galactose, and sialic acid, and n is an integer from 0 to 10, and in which the reducing-end terminal sugar unit is either a hemiacetal or is glycosidically bound to a carrier CA;

R²⁰ is a group of the formula I'

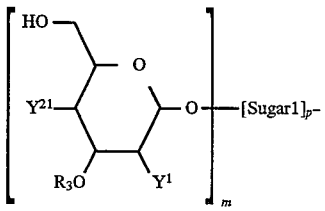

in which m is an integer 0 or 1;
p is an integer from 1 to 5;
Sugar1 is a monosaccharide unit selected from the group consisting of D-glucose, D-galactose, D-mannose, D-xylose, D-ribose, D-arabinose, L-fucose, 2-acetamido-2-deoxy-D-glucose, 2-acetamido-2-deoxy-D-galactose, D-glucuronic acid, D-galacturonic acid, D-mannuronic acid, 2-deoxy-2-phthalimido-D-glucose, 2-deoxy-2-phthalimido-D-galactose, and sialic acid; and R³ is H or a sialic acid residue of the formula II defined above in which $Z^1$, $R^1$, $Y^{10}$, $Y^{20}$, $Y^{30}$ and $Z^2$ are as defined above, and $X^1$ and $Y^1$ together form a bond and $Y^{21}$ is —OH, or $X^1$ and $Y^{21}$ together form a bond and $Y^1$ is —OH or —NHAc.

As it will be seen, the compounds of the present invention are lactam analogs of corresponding ganglioside lactones, and such lactams are highly stable at neutral pH and should provide a good lactone substitute. Thus, in the case of $GM_3$-lactone it has been shown (as it will be discussed below) that the corresponding $GM_3$-lactam has an extremely similar over-all shape compared to the lactone which means that the lactam is potentially able to induce the production of antibodies that will cross-react with the corresponding ganglioside lactone and in turn elicit an immune response directed against the ganglioside lactone and thereby against entities on which the ganglioside lactone are present.

DETAILED DESCRIPTION OF THE INVENTION

As it will appear from the definition above, the group $(Sugar)_n$ and the group $[Sugar1]_p$ is a group consisting of n and p monosaccharide units, respectively, each of which are selected from those listed. It will be apparent from formula I that the Sugar unit closest to the ring in formula I is glycosidically linked (α or β). Likewise, the Sugar1 unit closest to the ring in formula I, i.e. the unit bound to the 6-position of the ring, is glycosidically linked (α or β). The entire group $(Sugar)_n$ or $[Sugar1]_p$ may be straight-chain or branched, meaning that the aggregate of units in the entire group may form a straight chain or a branched chain. Generally speaking, it is preferred that each unit (apart from the reducing-end terminal unit) is bound to a subsequent unit via a glycosidic linkage (α or β). The glycosidic linkage may connect to any of the available positions in the subsequent unit, e.g. the 2-, 3-, 4- or 6-positions of the common saccharide units or simple derivatives thereof or the 8-position of sialic acid.

Furthermore, as also defined above, the reducing-end terminal saccharide unit in the group $(Sugar)_n$ may be either a hemiacetal, i.e. be unsubstituted, or it may be glycosidically bound (α or β) to a carrier CA. Similarly, the ring in formula I may also be glycosidically bound to a carrier CA, namely when $R^{10}$ is such a carrier.

A carrier CA may be any of the aglycon groups that are found in natural or synthetic glycoconjugates, glycosides (soluble or insoluble), glycolipids or glycoproteins (as also discussed and exemplified in e.g. G. Magnusson et al. *J. Org. Chem.* 1990, 55, 3932).

Thus, such an aglycon may be a lipid group, i.e. a lipophilic group which together with the carbohydrate moiety forms a glycolipid. Examples of such lipid groups are an acyl group of a fatty acid, e.g. a fatty acid with a saturated or unsaturated, branched or unbranched hydrocarbon chain of 1–25 carbon atoms such as $C_{1-20}$ alkanoic and alkenoic acids, an aryl-containing group such as a benzoyl, phenyl or benzyl group, or asteroid group such as a cholesterol or lanosterol group. Other examples of lipid groups are a sphingolipid or glycerolipid group. The glycosphingolipids or glycoglycerolipids arising as a result of the coupling with the terminal Sugar unit have the following general structures

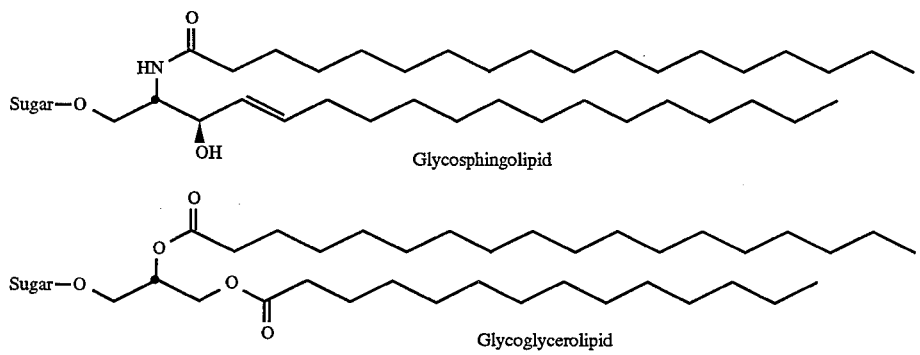

Other lipid groups that can be coupled to the terminal Sugar unit may be one of the aglycon groups described in U.S. Pat. No. 4,868,289 which is hereby incorporated by reference. Such aglycon groups may preferably be the sulphur-containing aglycons of the general formula

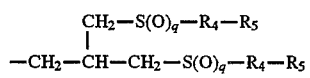

where q is an integer 0, 1, or 2, $R_4$ is a saturated or unsaturated, branched or unbranched alkyl chain of 1–25 carbon atoms, an aryl or asteroid group, and $R_5$ is H or a functional group such as CHO, $NO_2$, $NH_2$, OH, SH, COOH, or $CONH_2$. However, the functional group, in particular COOH or $CONH_2$, may further be bound to a large or macromolecular structure as defined below.

The carrier CA may further be a large or macromolecular structure which may be any organic or inorganic, polymeric or otherwise macromolecular structure, examples of which are residues of proteins, polysaccharides, plastic polymers and inorganic materials. Residues of proteins are preferably bound through nucleophilic groups in the proteins, e.g. amino, hydroxy, or mercapto groups. The proteins themselves may be any of a wide variety of proteins, in particular biologically compatible proteins such as globulins, albumins such as ovalbumin, bovine serum albumin (BSA) and human serum albumin (HSA), fibrins, polylysin, "keyhole" limpet hemocyanin (KLH), tetanus toxoid, etc. The polysaccharides may be any of a wide variety of polysaccharides and may be bound through hydroxy groups on ordinary polysaccharides such as cellulose, starch or glycogen, through amino groups on aminosaccharides such as chitosane or aminated sepharose, and through mercapto groups on thiomodified polysaccharides. Examples of plastic polymers are aminated or thiolated latex, thiolated, aminated, or hydroxylated polystyrene, and polyvinyl alcohol. Examples of inorganic materials are aluminum oxide, or silicon oxide materials such as silica gel, zeolite, diatomaceous earth, or the surface of various glass or silica gel types such as thiolated or aminated glass, where the glass may be in the form of e.g. beads.

Specific examples of carriers CA are illustrated below as they are attached to the reducing-end terminal sugar unit.

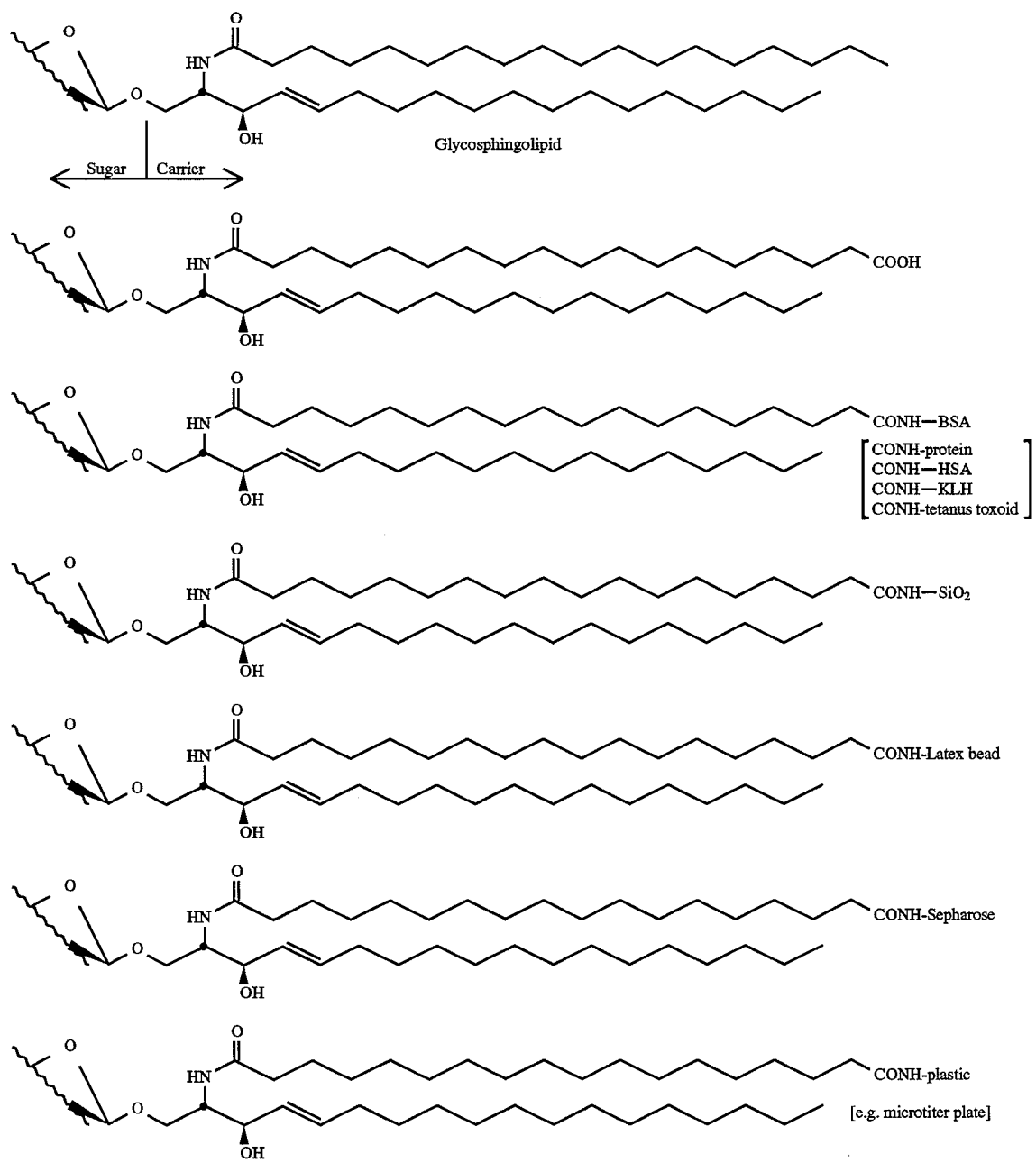

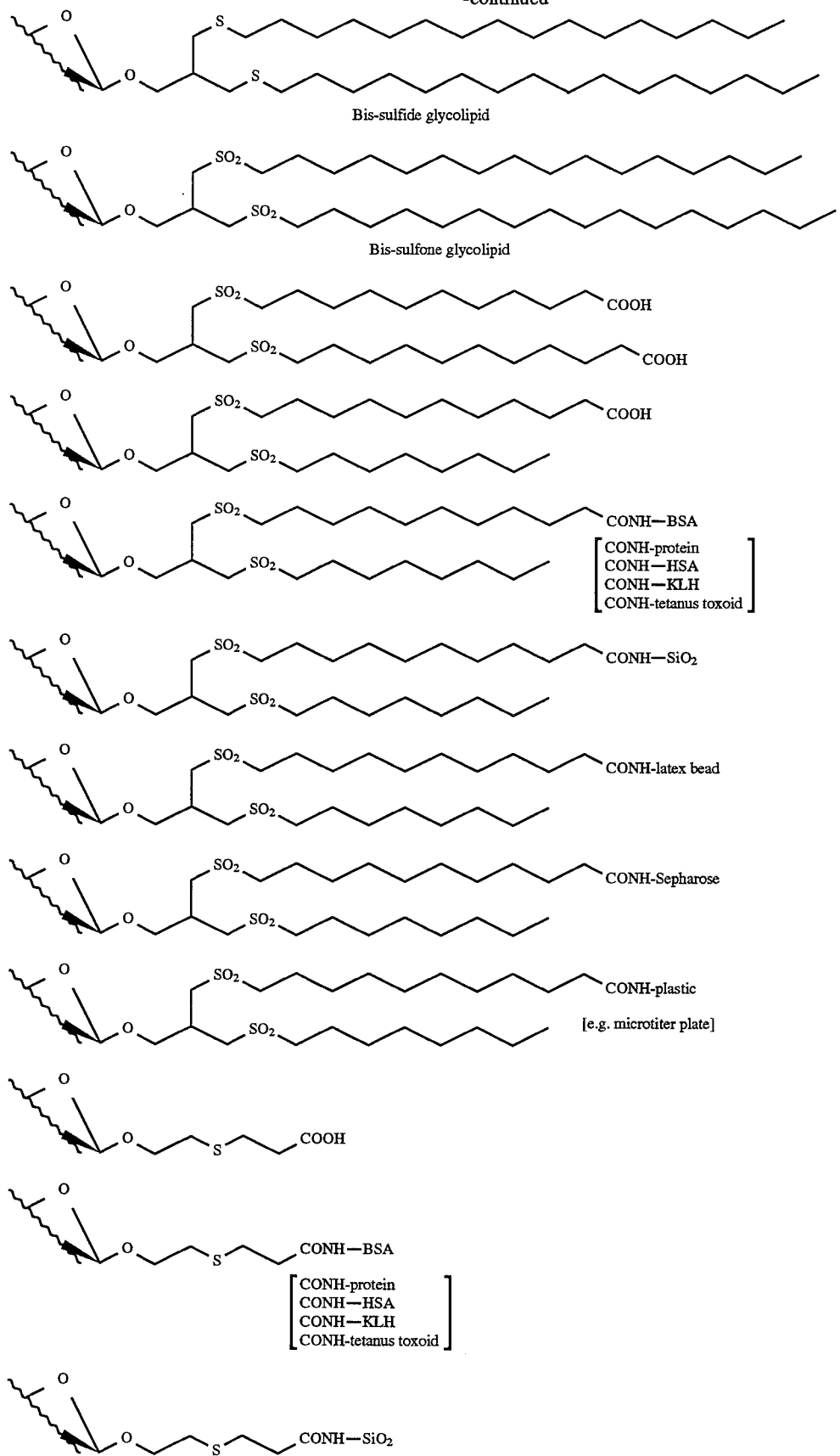

-continued
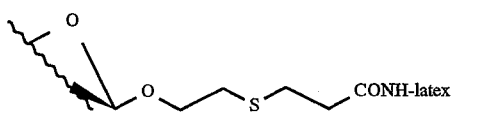
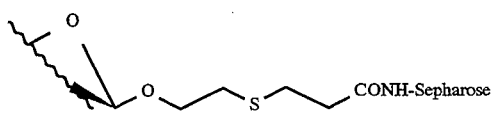
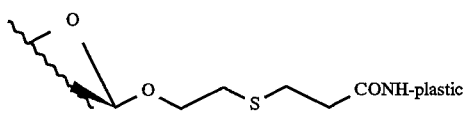
[e.g. microtiter plate]
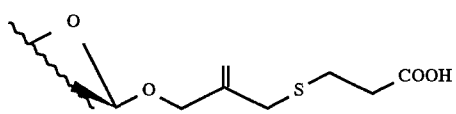
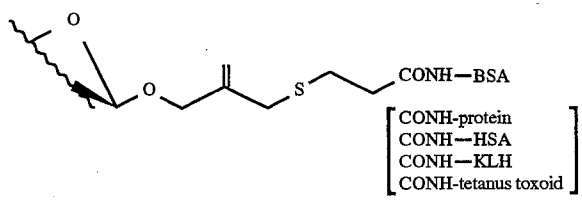
⎡ CONH-protein ⎤
⎢ CONH—HSA ⎥
⎢ CONH—KLH ⎥
⎣ CONH-tetanus toxoid ⎦
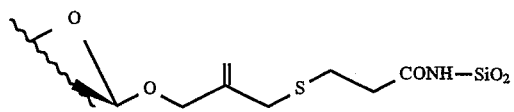
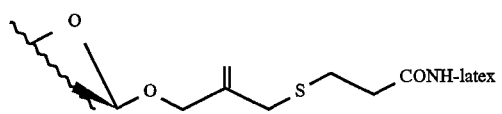
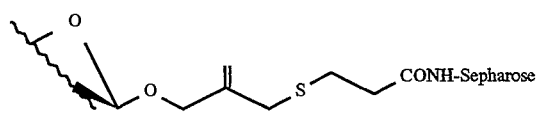
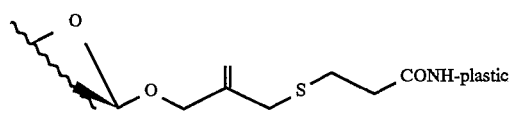
[e.g. microtiter plate]

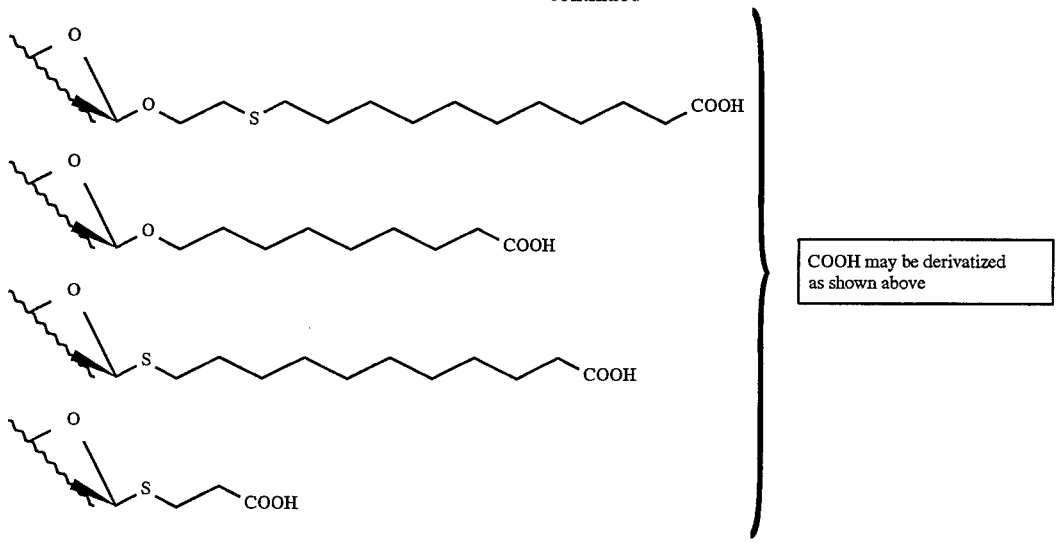

COOH may be derivatized as shown above

Preferred compounds of the invention are those in which at the most one of $Y^2$ and $Y^3$ is a group —$OR^{20}$.

Among those compounds, particularly preferred compounds are those in which $Y^3$ is —OH and each Sugar unit in $R^{10}$, if present, as well as the ring structure and each Sugar1 unit in the formula I', if present, are selected from D-glucose, D-galactose, 2-acetamido-2-deoxy-D-galactose, and L-fucose units. In such compounds, it is especially preferred that the ring in the general formula I has the galacto configuration. Also, it is further preferred that $R^1$ is H.

It is clear that for each of the two sialic acid residues of formula II and III, there are two possible ways for the acid group on the sialic acid to form a lactam with positions on the ring in formula I and in formula II, respectively. Furthermore, a compound of the invention may, by virtue of the definition of $R^3$ in the group I', contain up to four sialic acid residues with the consequent number of possible lactamization sites. Furthermore, only at least one of the possible lactamization sites need participate in a lactam function. This results in a considerable number of possible specific structures for each basic ganglioside structure in terms of the nature of the various carbohydrate functions [the ring in formulas I and I', the nature of Sugar1, and the nature and composition of $(Sugar)_n$, as well as the remaining variables not involved in the lactam formation]. To illustrate this relationship, the scheme below shows the possible lactones (and the equilibrium reactions therebetween to which the lactones, unlike the lactams of the invention, are subject to) that can form from two gangliosides, namely (A) $GM_3$-ganglioside which contains one sialic acid unit, and (B) $GD_3$-ganglioside which contains two sialic acid units. The nomenclature used in the scheme and in the rest of the present application is derived from the standard nomenclature for the identification and characterization of gangliosides that is described in the literature, in particular *Methods in Enzymology*, vol. 179, part F, V. Ginsburg Ed., Academic Press Inc.

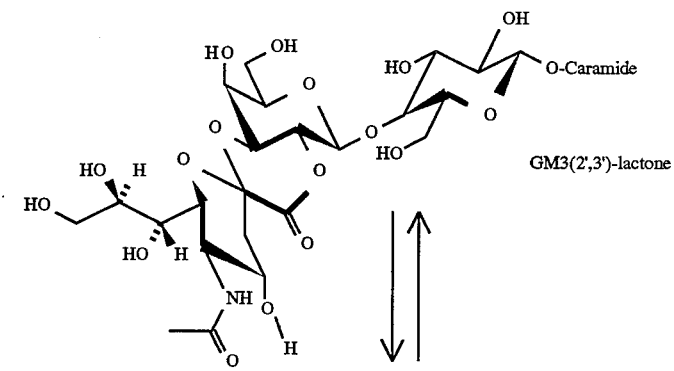

GM3(2',3')-lactone

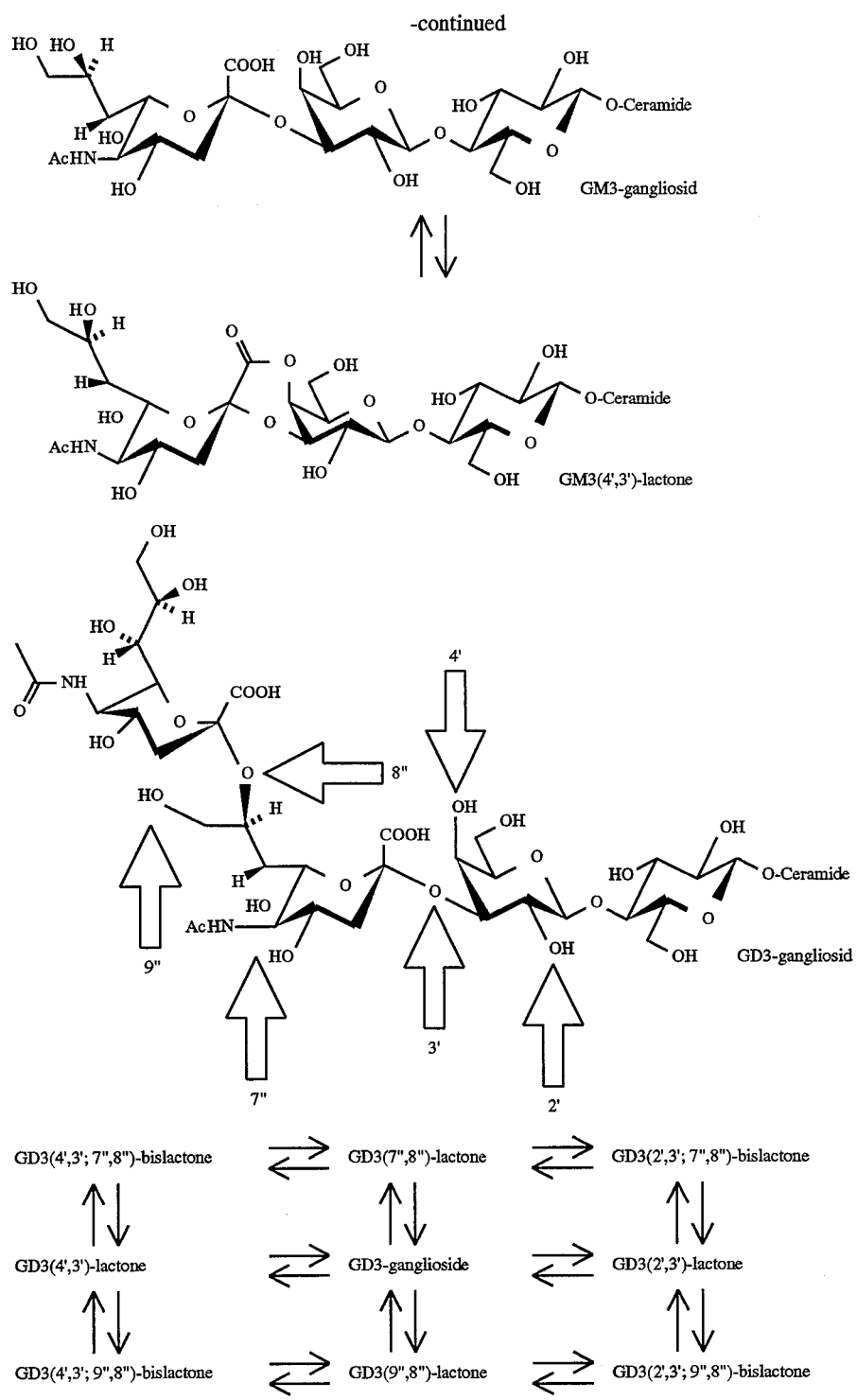
Examples of specific lactam structures are shown below where each compound is named based on the ganglioside from which it is derived and with the lactam functions indicated via the positions between which the lactam bridge is formed.

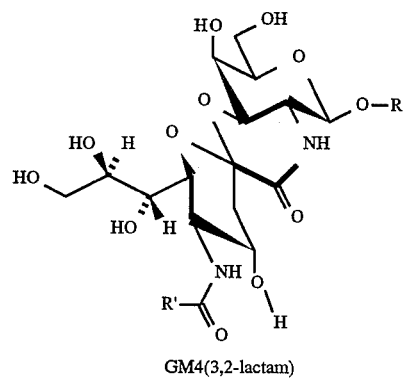
GM4(3,2-lactam)
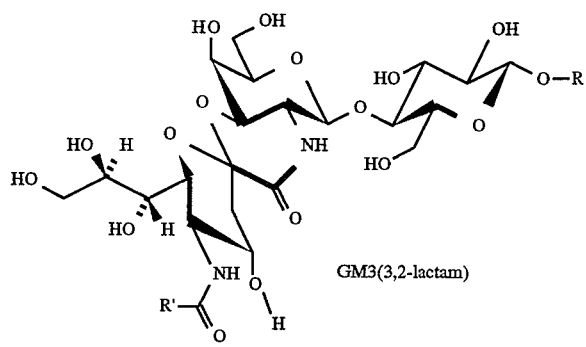
GM3(3,2-lactam)
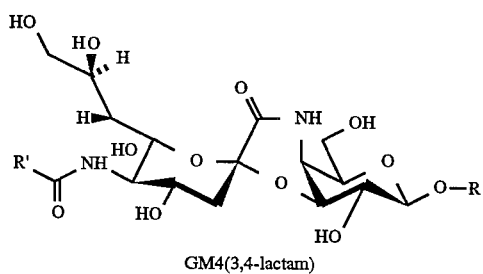
GM4(3,4-lactam)
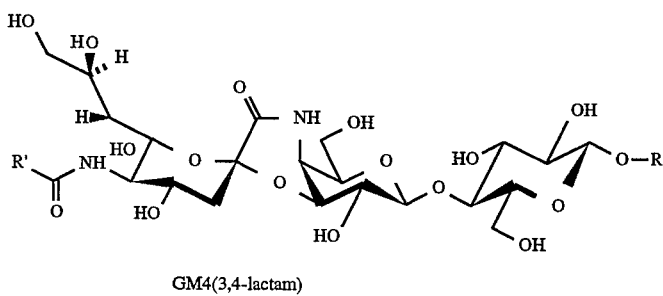
GM4(3,4-lactam)

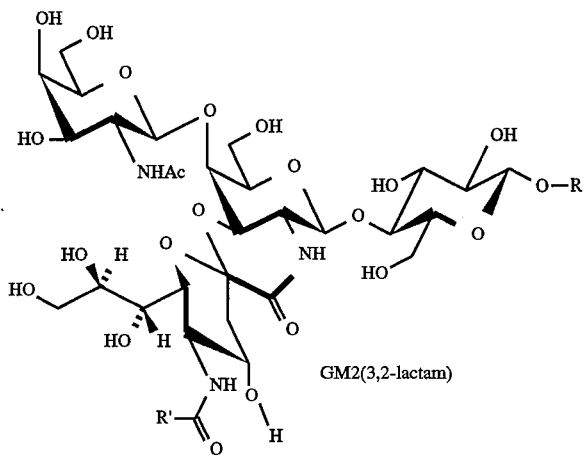
GM2(3,2-lactam)
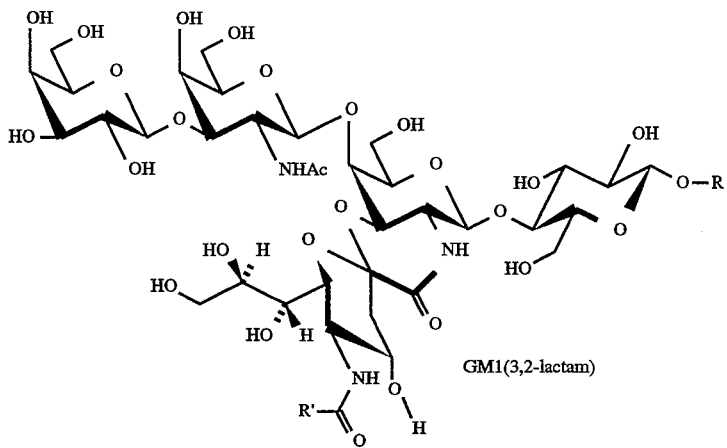
GM1(3,2-lactam)
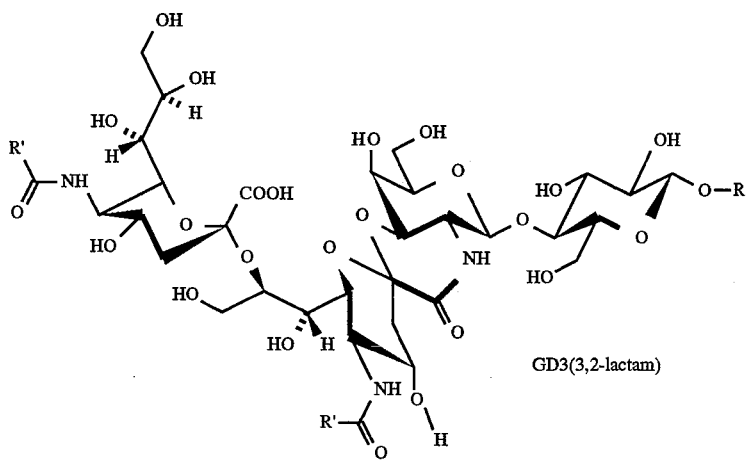
GD3(3,2-lactam)

-continued
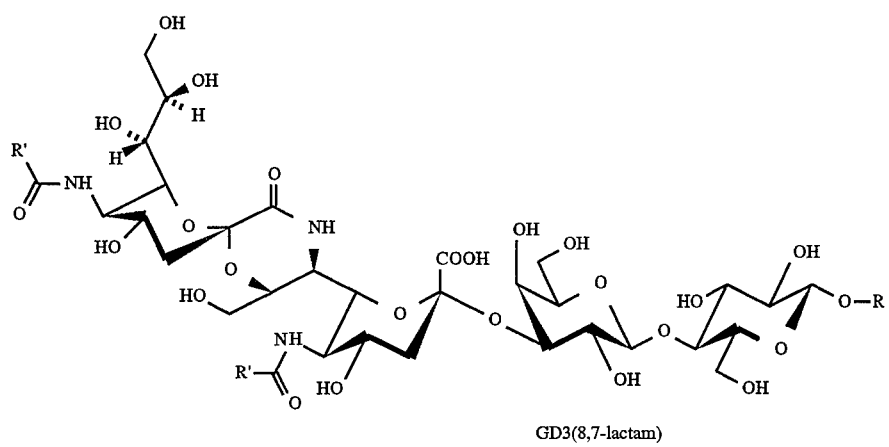
GD3(8,7-lactam)
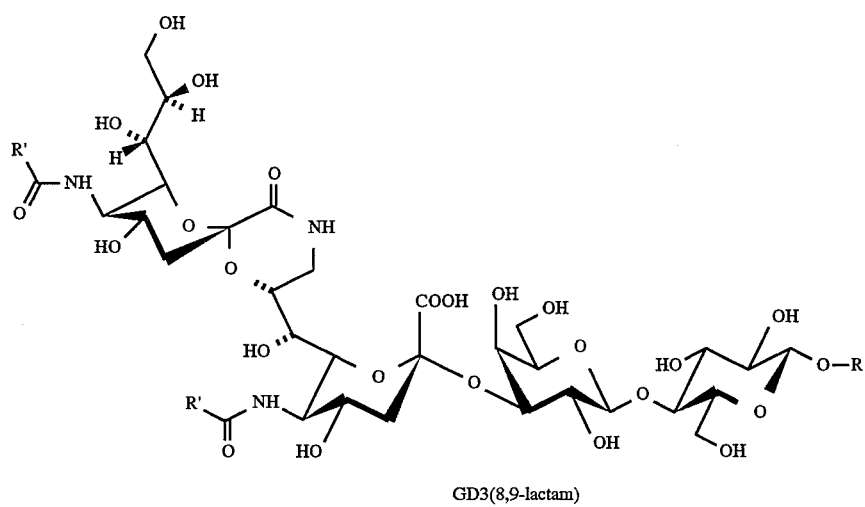
GD3(8,9-lactam)
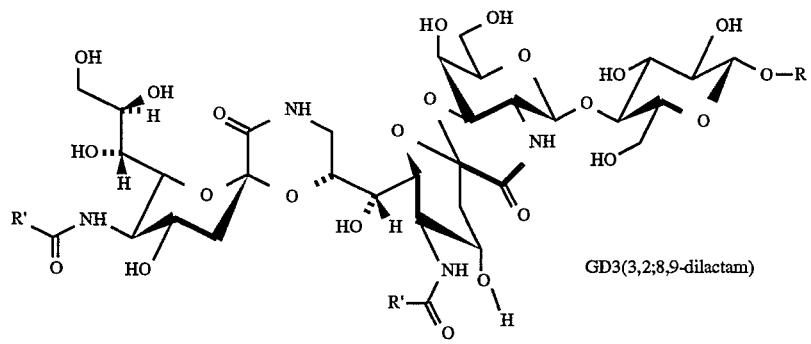
GD3(3,2;8,9-dilactam)

-continued
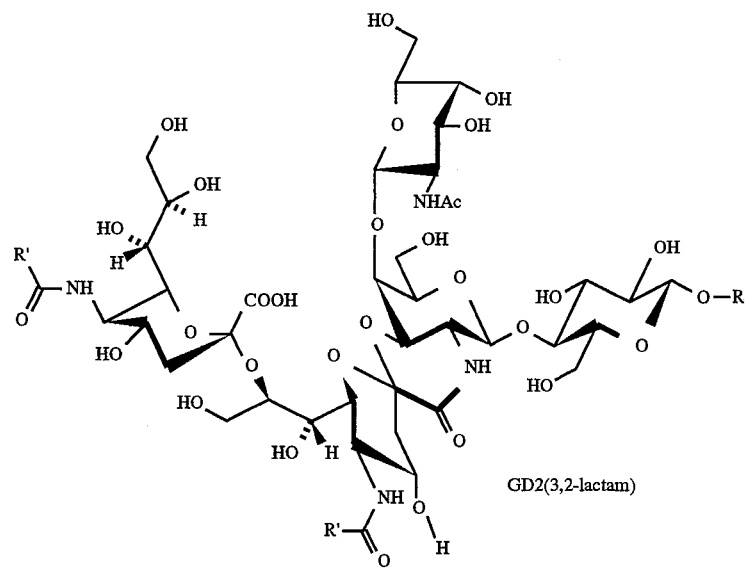
GD2(3,2-lactam)
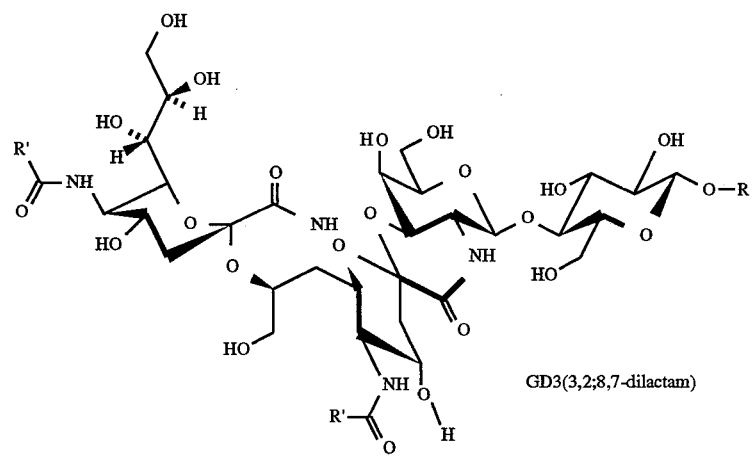
GD3(3,2;8,7-dilactam)
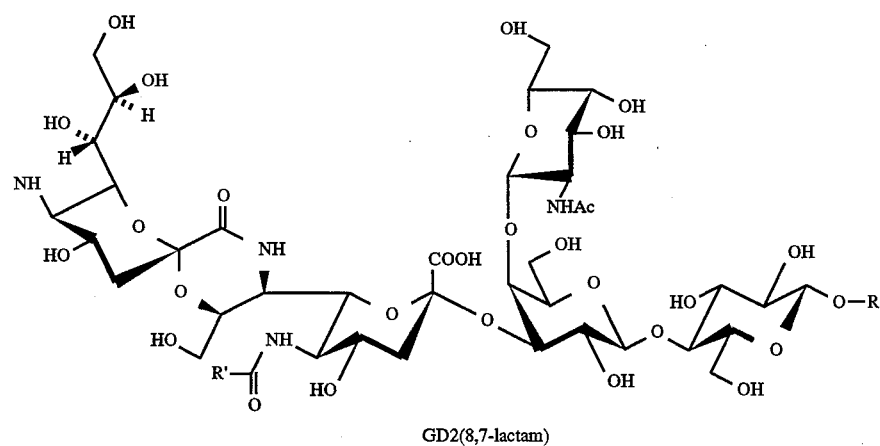
GD2(8,7-lactam)

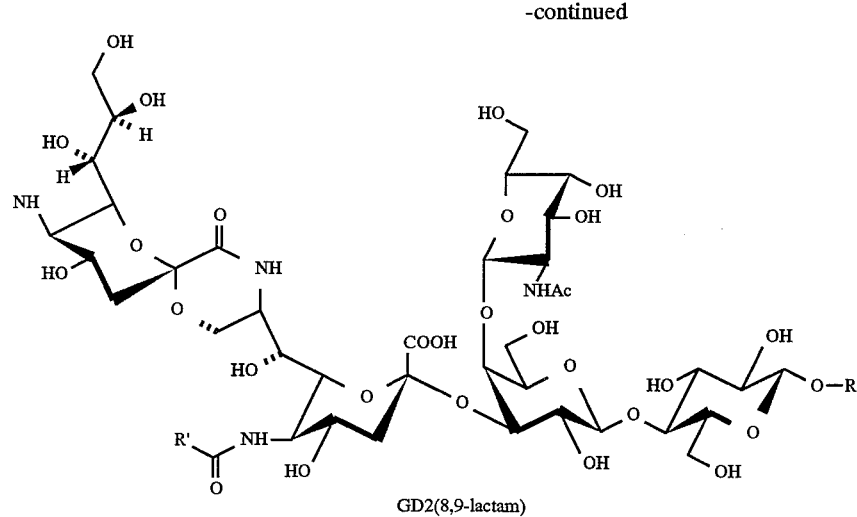
GD2(8,9-lactam)
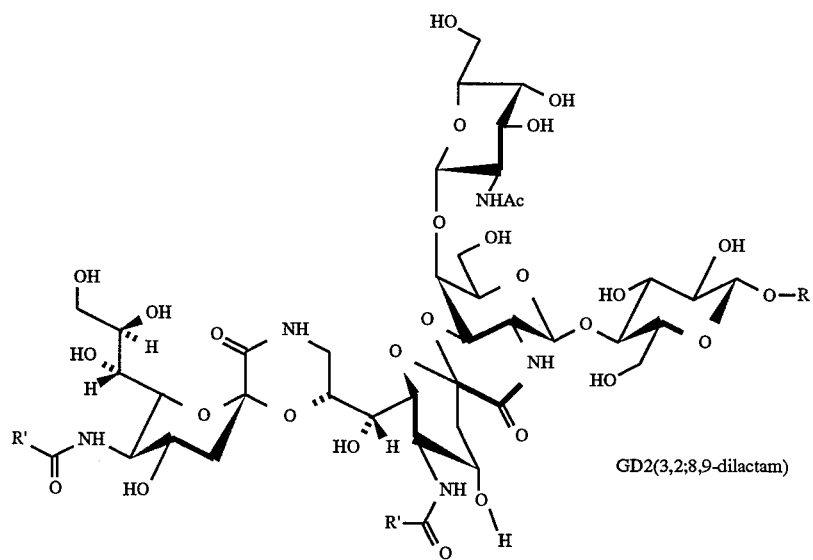
GD2(3,2;8,9-dilactam)
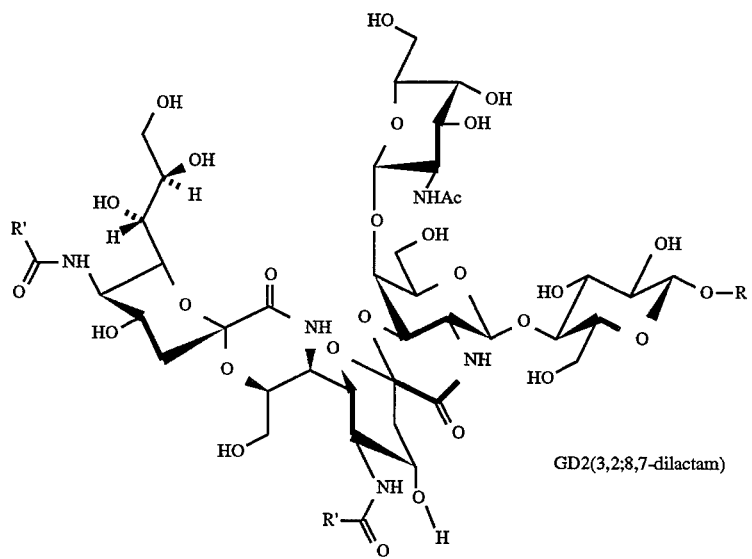
GD2(3,2;8,7-dilactam)

-continued
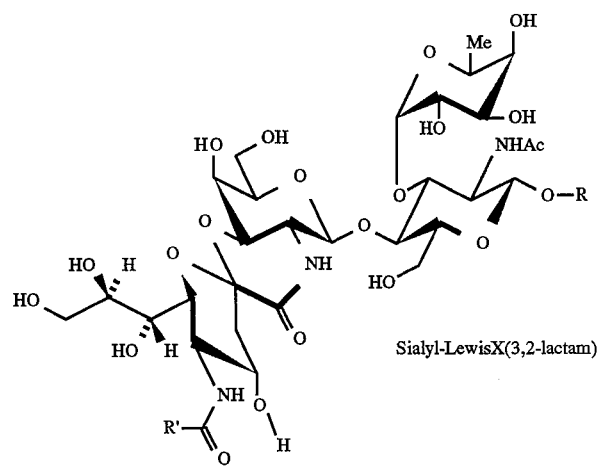
Sialyl-LewisX(3,2-lactam)
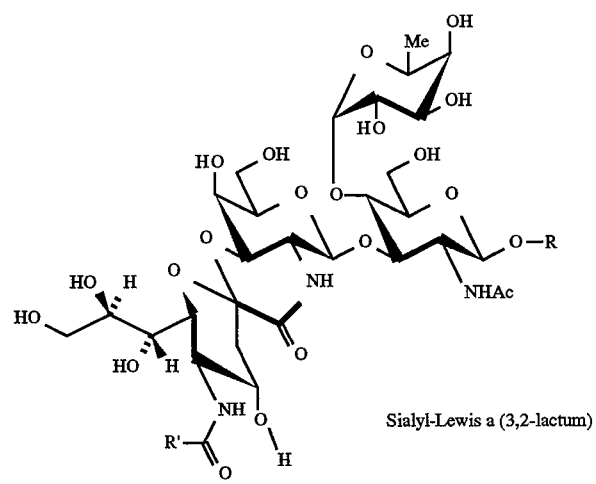
Sialyl-Lewis a (3,2-lactum)
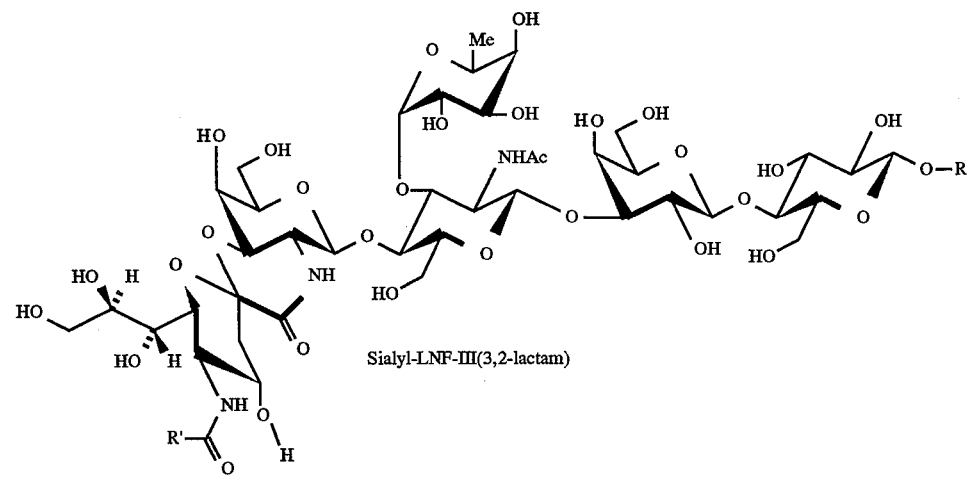
Sialyl-LNF-III(3,2-lactam)

-continued
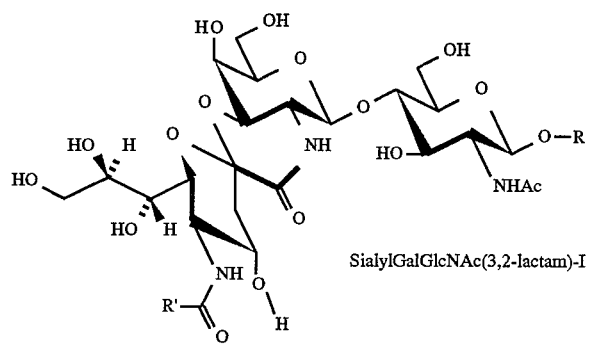
SialylGalGlcNAc(3,2-lactam)-I
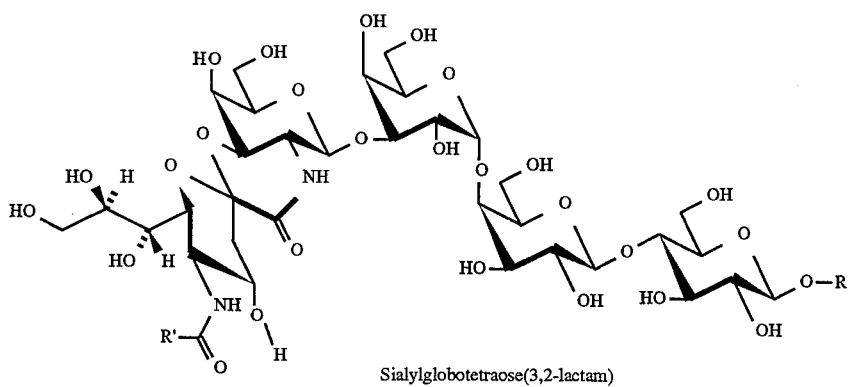
Sialylglobotetraose(3,2-lactam)
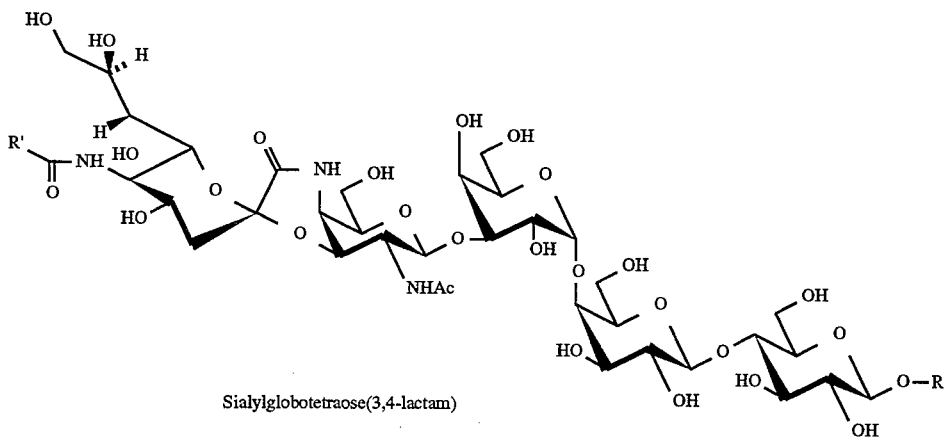
Sialylglobotetraose(3,4-lactam)
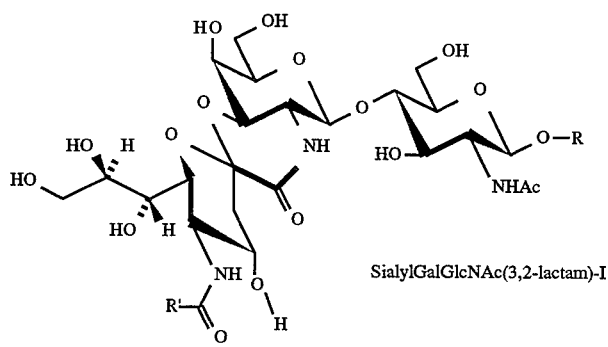
SialylGalGlcNAc(3,2-lactam)-I -continued
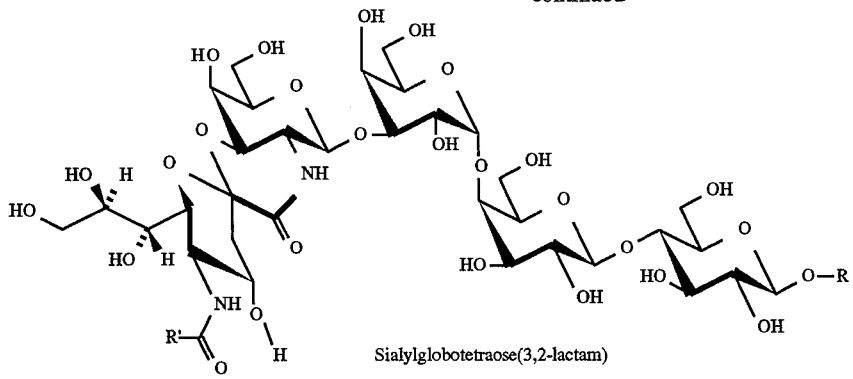
Sialylglobotetraose(3,2-lactam)
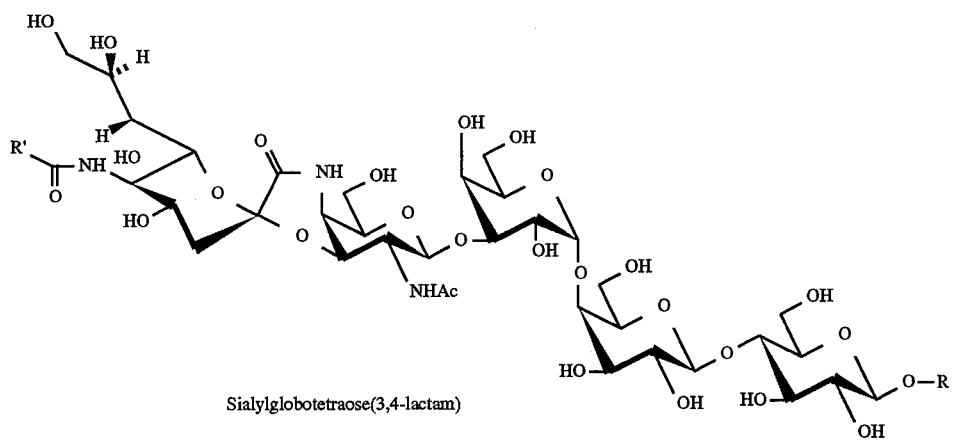
Sialylglobotetraose(3,4-lactam)
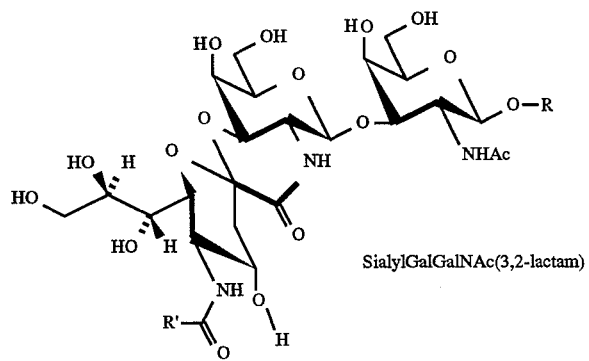
SialylGalGalNAc(3,2-lactam)
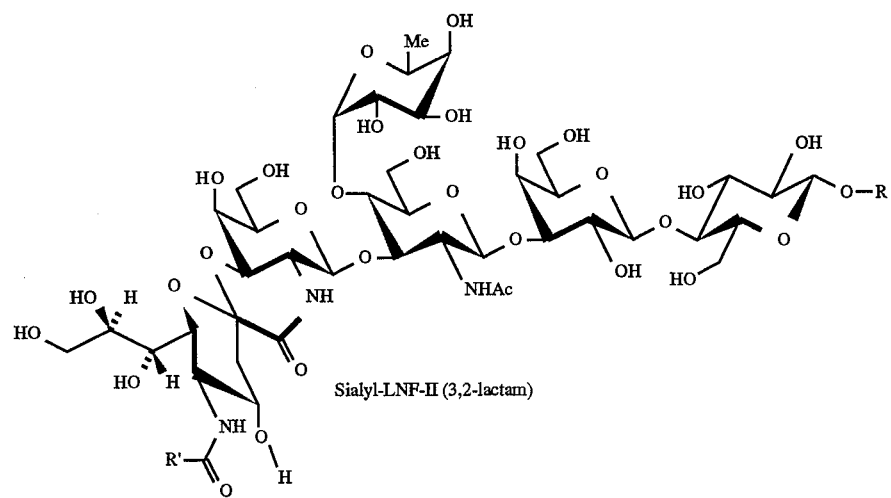
Sialyl-LNF-II (3,2-lactam)

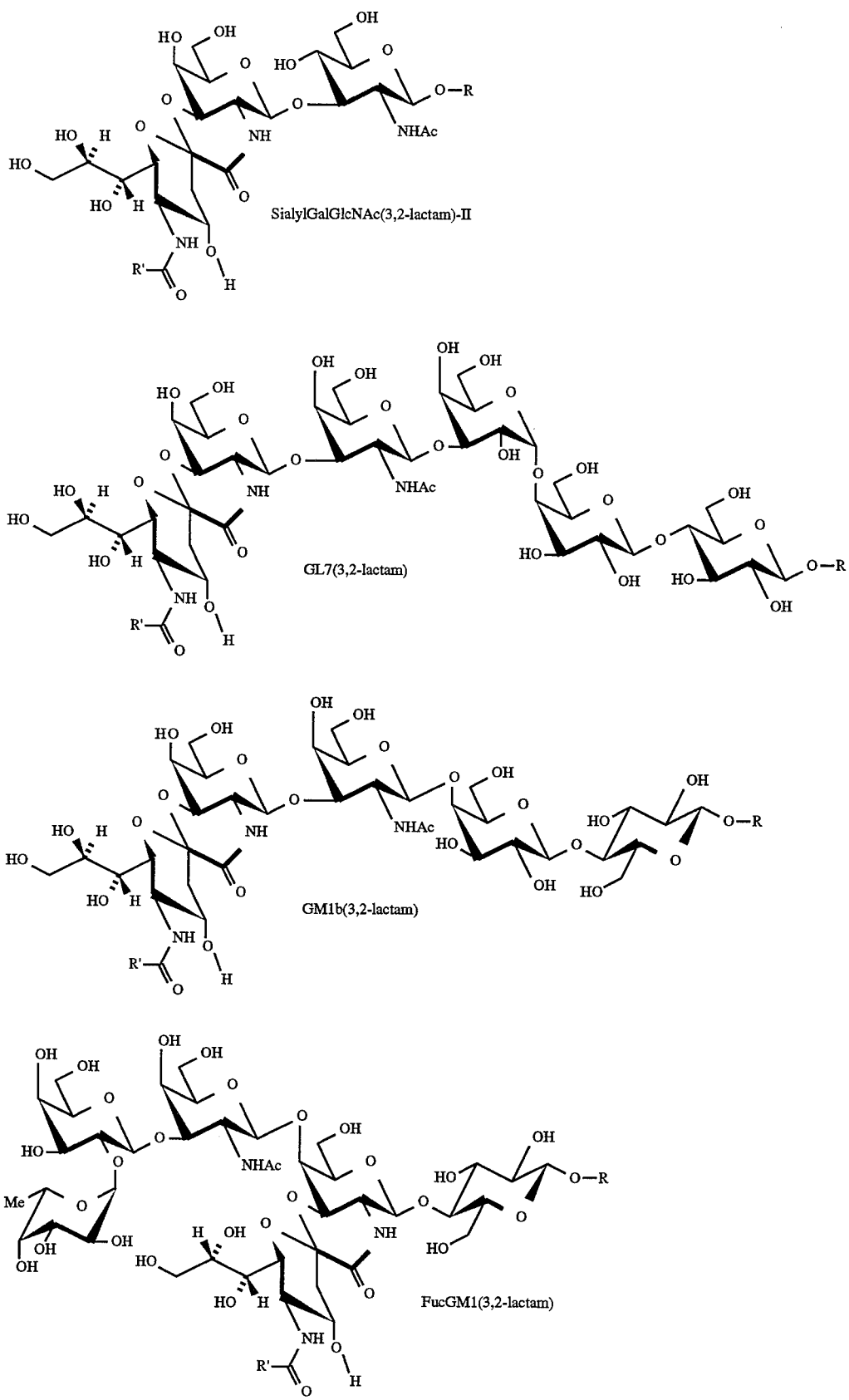

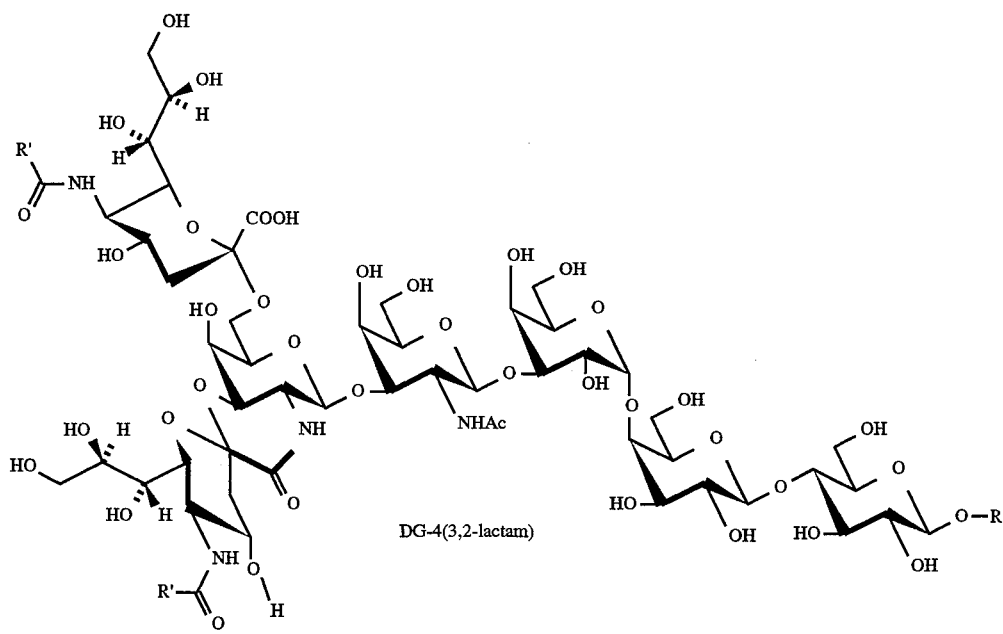
DG-4(3,2-lactam)
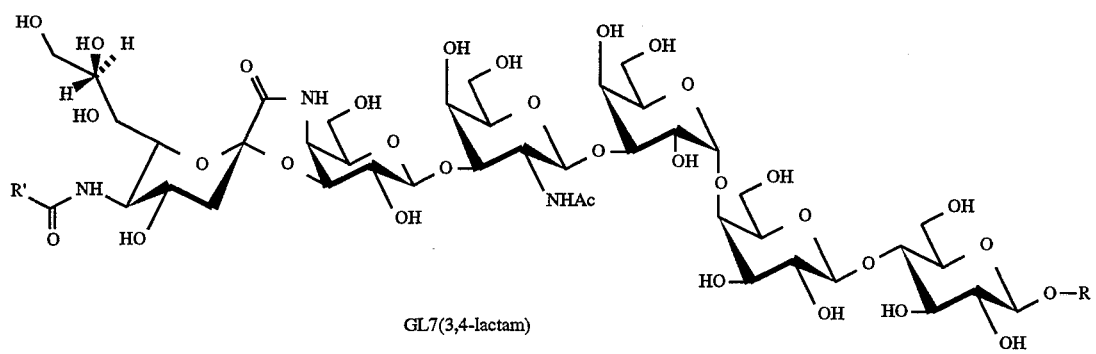
GL7(3,4-lactam)
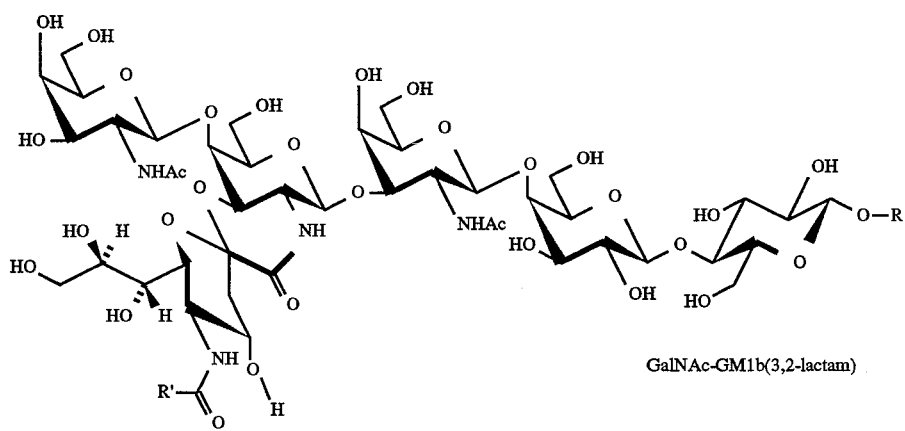
GalNAc-GM1b(3,2-lactam)

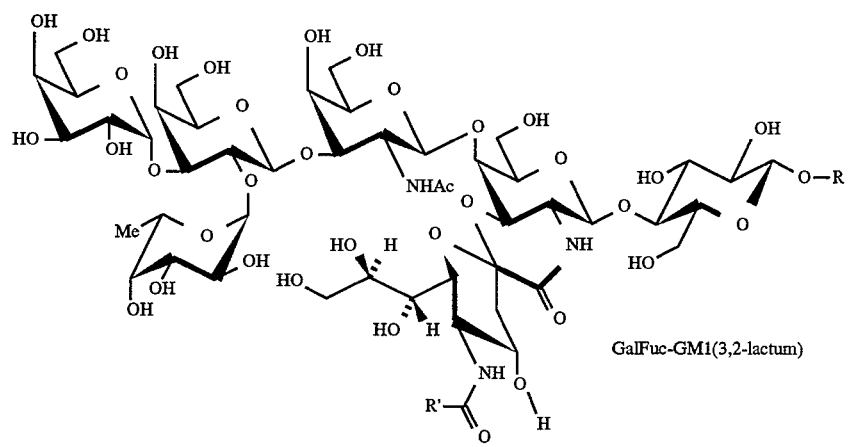
GalFuc-GM1(3,2-lactum)
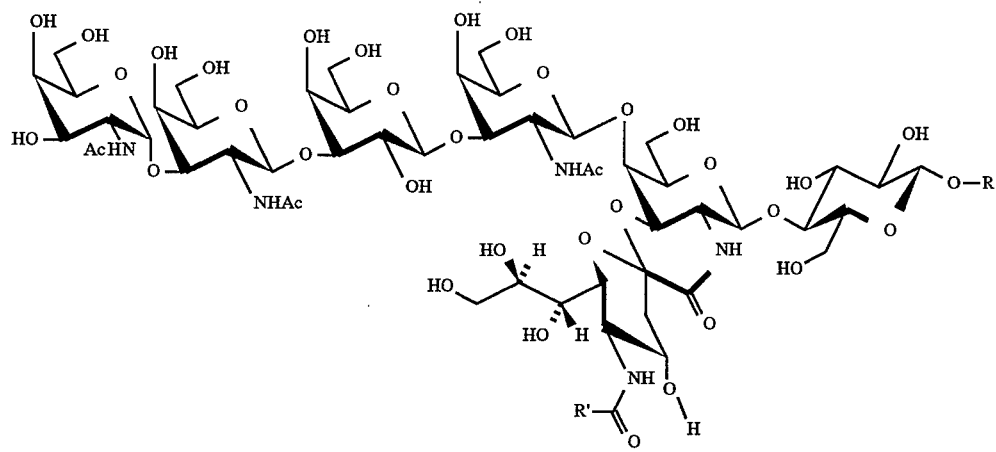
Forssman-GM1-combin.(3,2-lactam)
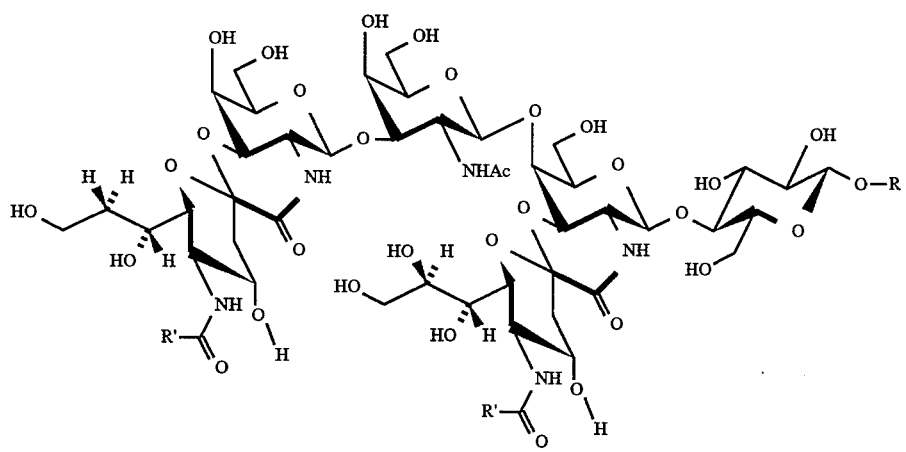
GD1a(3,2-dilactam)

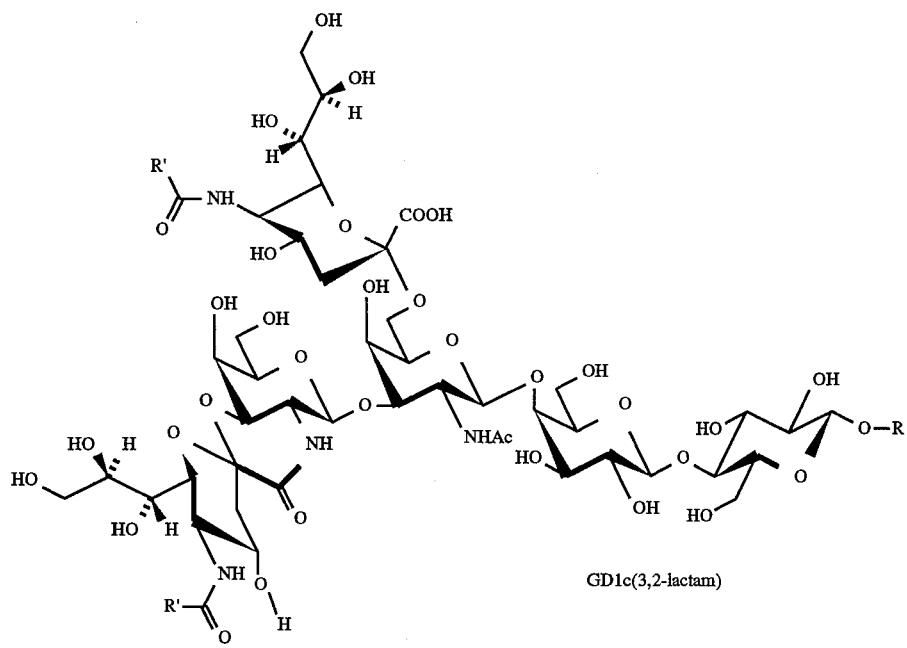
GD1c(3,2-lactam)
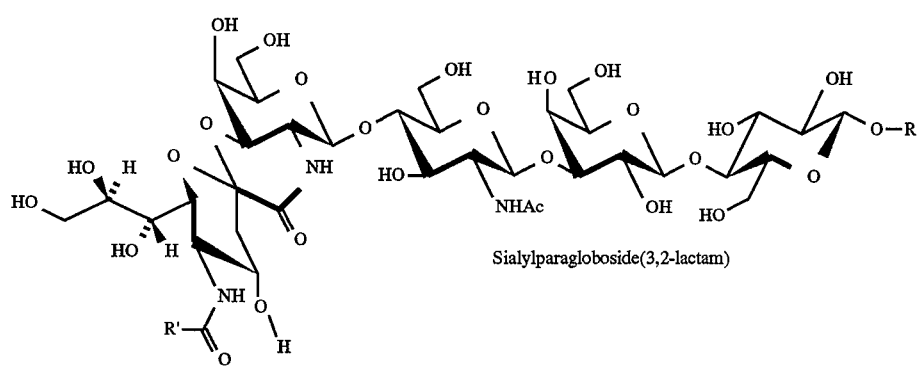
Sialylparagloboside(3,2-lactam)
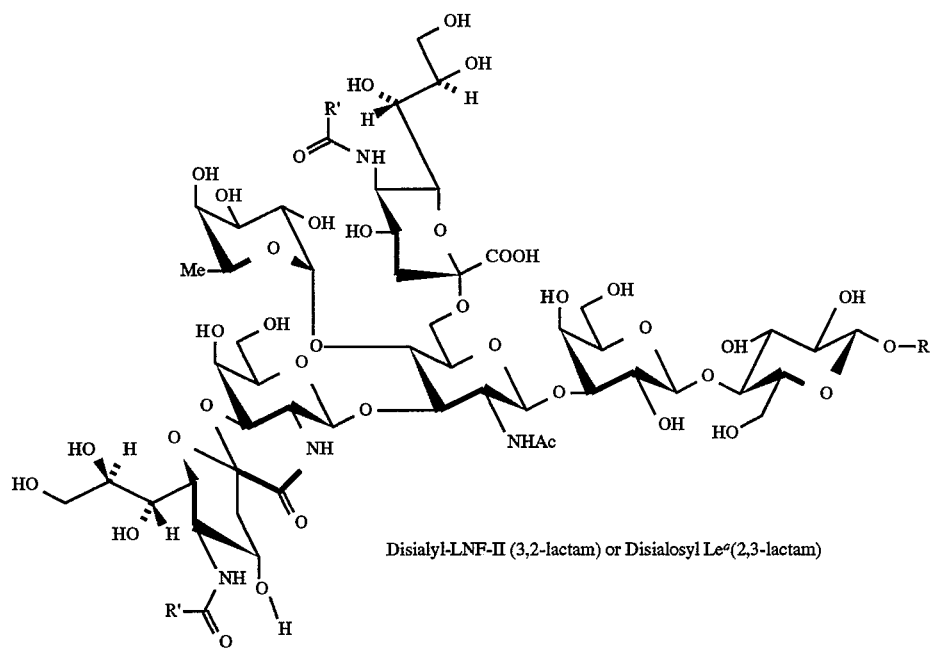
Disialyl-LNF-II (3,2-lactam) or Disialosyl Le$^a$(2,3-lactam)

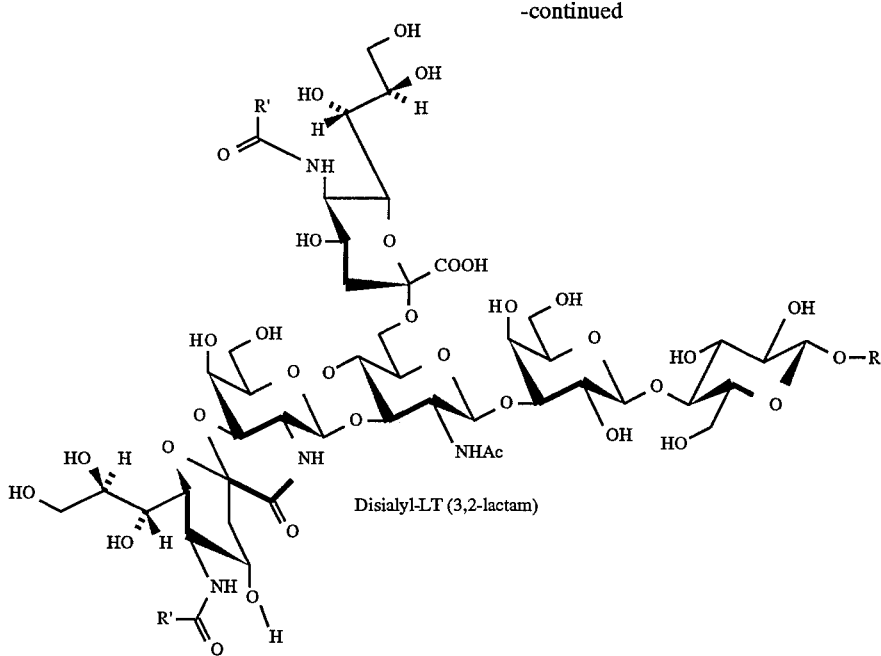

Disialyl-LT (3,2-lactam)

Generally speaking, the compounds of formula I according to the invention may, apart from the novel formation of the lactam rings, be prepared by standard and well-established reaction sequences and procedures for protection/deprotection and glycoside synthesis used in the preparation of oligosaccharide glycoconjugates described in the literature such as by G. Magnusson et al cited above. Lactam ring formation is usually performed after completion of the construction of the oligosaccharide chain, after which the aglycon carrier CA can be introduced. The nitrogen(s) that is/are to be part of the lactam ring(s) may be introduced in protected form at the monosaccharide level in the synthetic pathway and is then deprotected and activated for ring-closure with the carboxylic moiety of the sialic acid residue. Another and alternative route for the formation of lactam rings is based on employing peptidase-induced lactamization of NeuAcα2-3GalNAc residues where the N-acetyl group of GalNAc is removed by means of the peptidase enzyme, thus leading to ring-closure of the resulting free amino group with the carboxylic group of the NeuAc residue.

More specifically, the glycosylation reactions may be carried out in an aprotic, polar or non-polar organic solvent such as methylene chloride, toluene, acetonitrile, ether, or nitromethane. The reaction temperature is not critical and may range from −78° C. to +150° C., normally from 0° C. to 50° C. such as room temperature, although yield maximization may be obtained through temperature regulation. The reaction time may be from 0.1 to 200 hours, normally 1–24 hours such as 16 hours. The glycosyl donors may be halogeno sugars, sugar 1,2-orthoesters, 1-O-acyl sugars or thioglycosides, and promoters may be chosen from metal salts or other electrophilic reagents such as silver oxide, silver carbonate, silver triflate, $HgBr_2$, $Hg(CN)_2$, methylsulfenyl triflate, and dimethylthiomethylsulfonium triflate. Groups in the sugar derivatives that are sensitive to the reaction conditions may be protected. Thus, the hydroxy groups may be protected with acyl groups such as acetyl or benzoyl, with benzyl, or with a benzylidene group. The products formed may be purified by methods well known in the art such as extraction, crystallization or chromatography. The protecting groups may, if desired, subsequently be (selectively) removed by methods well known in the art, optionally followed by transformations of the deprotected positions and further purification.

The lactam nitrogen atom(s) may be introduced via the corresponding azide(s), which are present in the starting monosaccharide building blocks. Reduction of the azide to the amine may be carried out by treatment with sodium borohydride, optionally with addition of nickel chloride and boric acid, or by treatment with various thiols and hydrogen sulfide. The reduction may be carried out either before or after the glycosylation step that introduces a sialic acid residue. However, it is presently considered preferable to carry out the reduction late in the synthetic sequence, thereby avoiding protection of the amine formed. The reaction temperatures may range from −78° C. to +150° C., normally from −20° C. to +50° C., such as 0° C. The reaction time may be from 0.1 to 200 hours, normally 0.1–24 hours such as 20 minutes.

Ring closure of the lactam ring(s) may be carried out by treatment of an amino-sialic acid methyl ester-saccharide with a suitable solvent such as pyridine. With the presently known systems, additional catalysts (such as acids or bases) do no seem to be necessary; however, this might be needed in other cases. The reaction temperatures range from −78° C. to +150° C., normally from 0° C. to 50° C. such as room temperature. The reaction time may be from 0.1 to 200 hours, normally 0.1–24 hours such as 12 hours.

Conversion of the oligosaccharidic lactams into e.g. carrier glycosides may be carried out using the general methods described inter alia in the paper by G. Magnusson el al. cited above.

In another aspect, the present invention relates to an antibody which is directed against a compound of formula I described above. The antibody is preferably also capable of reacting with the corresponding ganglioside lactone.

The antibody is advantageously a monoclonal antibody since these tend to be of a higher specificity (i.e. a closer geometrical "fit" with the antigen and consequently a higher binding constant) than polyclonal antibodies, making them useful for accurate diagnostic determinations.

For purposes not requiring monoclonality, the antibody may be a polyclonal antibody. This may be prepared by injecting a suitable animal (e.g. a rabbit, monkey, sheep, mouse, goat, rat, pig, horse, or guinea pig) with a compound of the invention followed by one or more booster injections at suitable intervals (e.g. two weeks to a month) up to six months before the first bleeding. Then, while continuing this established immunization regimen, the animals are bled about one week after each booster immunization, and antibody is isolated from the serum in a conventional manner, e.g. as described in Harboe and Ingild, Scand. J. Immun. 2 (Suppl. 1), 1973, pp. 161–164.

The monoclonal antibody may also be produced by other conventional techniques (e.g. as described by Köhler and Milstein, Nature 256, 1975, p. 495) e.g. by use of a hybridoma cell line, or by clones or subclones thereof or by cells carrying genetic information from the hybridoma cell line coding for said monoclonal antibody. The monoclonal antibody may be produced by fusing cells producing the monoclonal antibody with cells of a suitable cell line, and selecting and cloning the resulting hybridoma cells producing said monoclonal antibody. Alternatively, the monoclonal antibody may be produced by immortalizing an unfused cell line producing said monoclonal antibody, subsequently growing the cells in a suitable medium to produce said antibody, and harvesting the monoclonal antibody from the growth medium. The cells producing the antibodies of the invention may be spleen cells or lymph cells, e.g. peripheric lymphocytes, from an immunized animal.

When hybridoma cells are used in the production of antibodies of the invention, these may be grown in vitro or in a body cavity of an animal. The antibody-producing cell is injected into an animal such as a mouse resulting in the formation of an ascites tumour which releases high concentrations of the antibody in the ascites of the animal. Although the animals will also produce normal antibodies, these will only amount to a minor percentage of the monoclonal antibodies which may be purified from ascites by standard purification procedures such as centrifugation, filtration, precipitation, chromatography or a combination thereof.

An example of a suitable manner in which the monoclonal antibody may be produced is as a result of fusing spleen cells from immunized mice (such as Balb/c mice) with myeloma cells using conventional techniques (e.g. as described by R. Dalchau, J. Kirkley, J. W. Fabre, "Monoclonal antibody to a human leukocyte-specific membrane glycoprotein probably homologous to the leukocyte-common (L-C) antigen of the rat", Eur. J. Immunol. 10, 1980, pp. 737–744). The fusions obtained are screened by conventional techniques such as binding assays employing the compounds of the invention.

For some purposes, it may be an advantage that the antibody is a hybrid antibody which contains a combining site directed against an epitope of the compound of the invention and further containing another combining site directed against another epitope of the same antigen, an epitope of another antigen or an epitope of a pharmaceutical. The term "combining site" is understood to mean the antigen recognition structure in the variable region of the antibody molecule. Hybrid antibodies make special procedures possible for detecting the antigen in a sample and for targeting a pharmaceutical or other biologically active molecule or another antigen to the site of the tumour where the reagent has the greatest effect. In an advantageous embodiment, the other antigen with which the hybrid antibody is reactive is a differentiation antigen of cytotoxic T-cells (cf. Staerz et al., Nature 314, 1985, p. 628). The pharmaceutical with which the hybrid antibody may be reactive is preferably selected from cytotoxic or antineoplastic agents (cf. Collier, R. J. and Kaplan, D. A., Scientific American 251, 1984, p. 44), see the discussion below.

The hybrid antibody may be produced by hybrids between two monoclonal cell lines producing the two relevant antibodies or may be produced by chemically linking fragments of the two antibodies.

The invention further relates to an antibody which, for various purposes, vide below, is an anti-idiotypic antibody, i.e. an antibody directed against the site of an antibody which is reactive with an epitope on the antigen, i.e. the compound of the invention. The anti-idiotypic antibody is directed against an antibody which is reactive with the compound of the invention. The anti-idiotypic antibody may be prepared by a similar method to that outlined above for the monoclonal or polyclonal antibody. The invention also relates to an anti-anti-idiotypic antibody directed against the anti-idiotypic antibody defined above.

An antibody directed against a compound of the invention as well as an anti-anti-idiotypic antibody defined above may in principle be used in the purification of compounds of formula I or of the anti-idiotypic antibodies described above by affinity chromatography.

In a further important aspect, the present invention relates to a diagnostic agent which comprises a compound of formula I as described above, an antibody of the invention as described above, an anti-idiotypic antibody as described above, or an anti-anti-idiotypic antibody as described above.

An antibody directed against the compound of the invention as well as an anti-anti-idiotypic antibody defined above may be used for in vitro diagnosis of cancer. Thus, for instance a biopsy sample may be treated with the antibody or anti-anti-idiotypic antibody followed by detection of bound antibody as described below. The anti-idiotypic antibody may, like the compound of formula I of the invention itself, be used to detect the presence in body fluids of an antibody against the compounds of the invention and thus to assess the strength of an immune response or whether further antibody treatment is necessary.

It is preferred for most purposes to provide the antibody with a label in order to detect bound antibody. In a double antibody ("sandwich") assay, at least one of the antibodies may be provided with a label in a well-known manner. Substances useful as labels in the present context may be selected from enzymes, fluorescent substances, radioactive isotopes and ligands such as biotin.

It should be noted that practically all methods or applications based on intact antibodies could instead be performed using fragments of the antibodies, e.g. $F(ab')_2$ or Fab fragments (cf. Delaloye, B. et al., J. Clin. Invest. 87, 1986, p. 301).

The invention further relates to a vaccine which comprises a compound of formula I according to the invention and a physiologically acceptable excipient or adjuvant. In connection with use in such vaccines, in it is preferred that the compound of the invention is one in which $R^{10}$ is a carrier CA or a group $(Sugar)_n$ as defined above and in which the reducing-end terminal sugar unit is glycosidically bound to a carrier CA. In particular, it is preferred that the carrier CA comprises a protein carrier or is a lipid group as described above.

Generally speaking, the vaccine should be made so as to allow an optimal stimulation of the relevant parts of the immune system, i.e to present the immunogenic agent for a period of time and in a form being optimal with respect to the recognition, the uptake or any other interaction or processing necessary for the stimulation.

If the carrier CA is a lipid group, a particularly interesting embodiment of the vaccine is that in which the compound of formula I forms part of a supramolecular aggregate. The term "supramolecular aggregate" is intended to mean suspensions, colloids, emulsions, or solutions (depending on size) of particles on whose surface the compound of the invention is located in a manner where it is able to interact with the surrounding environment so as to enable the immune system to detect its presence and to elicit an immune response. It is contemplated that the particles may be any of a number of especially biodegradable structures such as biodegradable polysaccharide particles, e.g. dextran particles, "liquid" particles comprising membranes consisting of surfactant layers having the compound of formula I embedded in the fluid membrane. Examples of such "liquid" particles are liposomes, micelles, or cubic phase particles.

In yet another aspect, the invention relates to a pharmaceutical composition for the treatment of human carcinoma having ganglioside lactones as carcinoma-associated antigens, which comprises an antibody according to any of claims 10–16 and a pharmaceutically acceptable excipient.

The excipient employed in the composition of the invention may be any pharmaceutically acceptable vehicle. This vehicle may be any vehicle usually employed in the preparation of injectable compositions, e.g. a diluent, suspending agent etc. such as isotonic or buffered saline. The composition may be prepared by mixing a therapeutically effective amount of the antibody with the vehicle in an amount resulting in the desired concentration of the antibody in the composition.

In some cases it may be advantageous to couple the antibody to a carrier, in particular a macromolecular carrier. Such macromolecular carriers may be any of those described above in connection with the compounds of the invention. Thus, the macromolecular carrier is usually a polymer to which the toxin is bound by hydrophobic non-covalent interaction, such as a plastic, e.g. polystyrene, or a polymer to which the antigen or antibody is covalently bound, such as a polysaccharide, or a polypeptide, e.g. bovine serum albumin, ovalbumin or keyhole limpet hemocyanin. Furthermore, the macromolecular carrier may advantageously be selected from a pharmaceutical, e.g. a cytotoxic or antineoplastic agent, to which the antibody is coupled. The macromolecular carrier may also be another antibody directed against a cytotoxic effector mechanism, e.g. cytotoxic cells. The macromolecular carrier should preferably be nontoxic and non-allergenic. The antibody may be multivalently coupled to the macromolecular carrier as this may provide an increased immunogenicity of the composition.

For oral administration, the composition may be in the form of a tablet, capsule, granulate, paste, gel, mixture or suspension optionally provided with a sustained-release coating or a coating which protects the antigen (i.e. the compound of the invention) from passage through the stomach.

Solid formulations, i.e. granulates, tablets and capsules, may contain fillers, e.g. sugars, sorbitol, mannitol and silicic acid; binders, e.g. cellulose derivatives such as carboxymethyl cellulose and polyvinylpyrrolidone; disintegrants, e.g. starch, sodium bicarbonate and calcium carbonate; lubricants, e.g. magnesium stearate, talc and calcium stearate. Semisolid formulations, i.e. pastes or gels, may comprise a gelling agent such as an alginate, gelatin, carrageenan, tragacanth gum and pectin, a mineral oil such as liquid paraffin, a vegetable oil such as corn oil, sunflower oil, rape oil and grape kernel oil, as well as a thickener such as a starch, gum, gelatin, etc. Liquid formulations, i.e. mixtures and suspensions, may comprise an aqueous or oily vehicle, e.g. water, or a mineral oil such as liquid paraffin, a vegetable oil such as corn oil, sunflower oil, rape oil, grape kernel oil, etc. The antigen of the invention may be suspended in the liquid vehicle in accordance with usual practice.

The sustained-release coating may, e.g., be an enteric coating which may be selected from shellac, cellulose acetate esters such as cellulose acetate phthalate, hydroxypropylmethyl cellulose esters such as hydroxypropylmethyl cellulose phthalate, polyvinyl acetate esters such as polyvinyl acetate phthalate, and polymers of methacrylic acid and (meth)acrylic acid esters.

In particular injectable compositions may be formulated using the types of particle suspensions, colloids, emulsions, or solutions described above in connection with the vaccine of the invention.

The composition may also be adapted for rectal administration, e.g. as a suppository. Such a suppository may contain conventional excipients such as cocoa butter or other glycerides.

Furthermore, the invention relates to the use of a compound according to the invention or an anti-idiotypic antibody of the invention for preparing a medicament for the treatment of human cancer, or to the use of an antibody or anti-antiidiotypic antibody according to the invention and for preparing a medicament for the treatment of human carcinoma.

Therapy of cancers, in particular carcinomas, the cells, in particular the cell membranes, of which comprise ganglioside lactones in concentrations higher than in normal cells may be carried out by a variety of procedures known to those skilled in the art. An antibody against the compounds of the invention (in particular a human monoclonal antibody for the reasons stated above) may be injected into cancer patients to combat the tumour directly or via various effector mechanisms, e.g. complement-mediated cytotoxicity or antibody-dependent cell-mediated cytotoxicity.

In another embodiment, the antibody may be utilized in a drug targeting approach. Thus, the antibody may be modified prior to injection into the patient as indicated above, e.g. by coupling to pharmaceuticals (thus transporting those to the site of their activity), or to another antibody directed against a cytotoxic effector mechanism such as antigens on cytotoxic T-cells or on other cytotoxic cells. It is contemplated that a hybrid antibody containing one combining site for the antigen compound of the invention and another combining site for another antigen or for a pharmaceutical as described above may also advantageously be used to provide a two-way attack on the tumour in question.

In principle, the targeting of the pharmaceutical may be carried out using either a hybrid antibody to which the pharmaceutical is already coupled by antigen-antibody-reaction or using a hybrid antibody which does not have any pharmaceutical coupled to it yet. In the first case, the antibody will upon administration seek out the ganglioside lactones on the cancer cell surfaces bringing the pharmaceutical with it whereupon the pharmaceutical will be able to exert its effect. In the second case, it will be necessary for the pharmaceutical to be administered separately, either before or after the antibody, and the antibody will then react with the pharmaceutical in the body on the surface of a cancer cell or in the blood stream.

The pharmaceutical which is coupled to the antibody may typically be an anti-cancer agent such an alkylating agent, e.g. melphalan, chlorambucil, busulfan, cisplatin, thiotepa, an antimetabolite such as methotrexate, fluracil, azathioprin, an antimitoticum, typically vincristine, vinblastine, or an antibiotic such as doxorubicin, daunorubicin or bleomycin. The medicament may also comprise bacterial or other toxins.

The compounds of the invention may be used for immunization in order to provoke an anti-cancer immune response in the body. For this reason, the invention further relates to a vaccine which comprises a compound of formula I according to the invention and a physiologically acceptable excipient. The compounds may further be used in vitro for raising effector cells against cancer by culturing the compound with e.g. leukocytes from a cancer patient.

It is further contemplated that the compounds or the pharmaceutical compositions of the invention may be used in a method of inhibiting cell-cell or cell-virus interaction, in particular in connection with bacterial or viral attachment to cells, inflammation, or metastasis of tumours, in human beings or animals comprising administering a compound or a pharmaceutical composition according to the invention. The basis for the method is the fact that one of the functions of gangliosides on cell surfaces is to function as receptors, and it is known that in interactions between on the one hand e.g. bacteria or viruses and on the other hand mammalian cells, gangliosides function as recognition receptors in that they interact with epitopes on the surfaces of the bacteria or viruses and help these entities to adhere to the cell surface or even to actually invade the cell. Thus, the administration of compounds of the invention may serve to "saturate" the epitopes on the bacteria, viruses or metastasis cells and may therefore result in a reduced ability of the epitopes to interact with the natural receptors.

The compounds of the invention may further be used in extra-corporal devices for removing circulating anti-tumour antibody or immune complexes or for purifying antibody preparations. Consequently, the invention also relates to a method of purifying antibodies according to the invention comprising contacting a solution containing the antibodies with a compound of the formula I with which the antibody is able to react, the compound being coupled to or comprising a solid support (such as the stationary phase, e.g. silica gel or dextran, in a affinity chromatographical process); removing the solution from the support; and releasing the antibody from the support. The release of the bound antibody from the support may be carried out by methods well known in the art, such as described by Maniattis et al., *Molecular Cloning: A Laboratory Manual*, Cold Spring Harbour, 1982, e.g. change in pH, salinity, or ionic strength, displacement with solutions of antigen-like compounds followed by dialysis, etc.

As a natural continuation of the possibility of using the compounds of the invention in a vaccine, the invention also relates to a method of treating or of boosting the immune protection against human cancer having ganglioside lactones as cancer-associated antigens, comprising administering a compound according to the invention in an amount capable of inducing the formation of antibodies against the compound.

The antibodies against the compounds of the invention may furthermore be administered to provoke an anti-idiotypic or anti-anti-idiotypic immune response. An anti-idiotypic antibody (whether monoclonal or polyclonal or a fragment of these) raised against an antibody reacting with the compounds of the invention may express epitopes similar to those of the antigen compound and may therefore be used in a similar fashion for immunization to elicit an anti-carcinoma immune response. Such antibodies may further be used in extra-corporal devices as described above for the primary antibody.

Anti-anti-idiotypic antibodies may be used in ways similar to those described for primary anti-tumour antibodies.

A further embodiment of a diagnostic method of the invention relates to a method of localizing tumours (in particular carcinomas) in vivo by means of the antibody of the invention. This method comprises administering a diagnostically effective amount of an antibody of the invention which is labelled so as to permit detection thereof, and determining the sites of localization of bound antibody. The antibody may be labelled by means of a radioactive isotope, in particular a physiologically tolerable isotope such as technetium, and subsequently injected and localized by known methods, e.g. a gamma ray detector of a suitable configuration (cf. Mach, J.-P. et al., *Nature* 248, 1974, p. 704).

BRIEF DESCRIPTION OF DRAWINGS

The invention is illustrated by the drawing, on which

EXAMPLES

Figure 1:
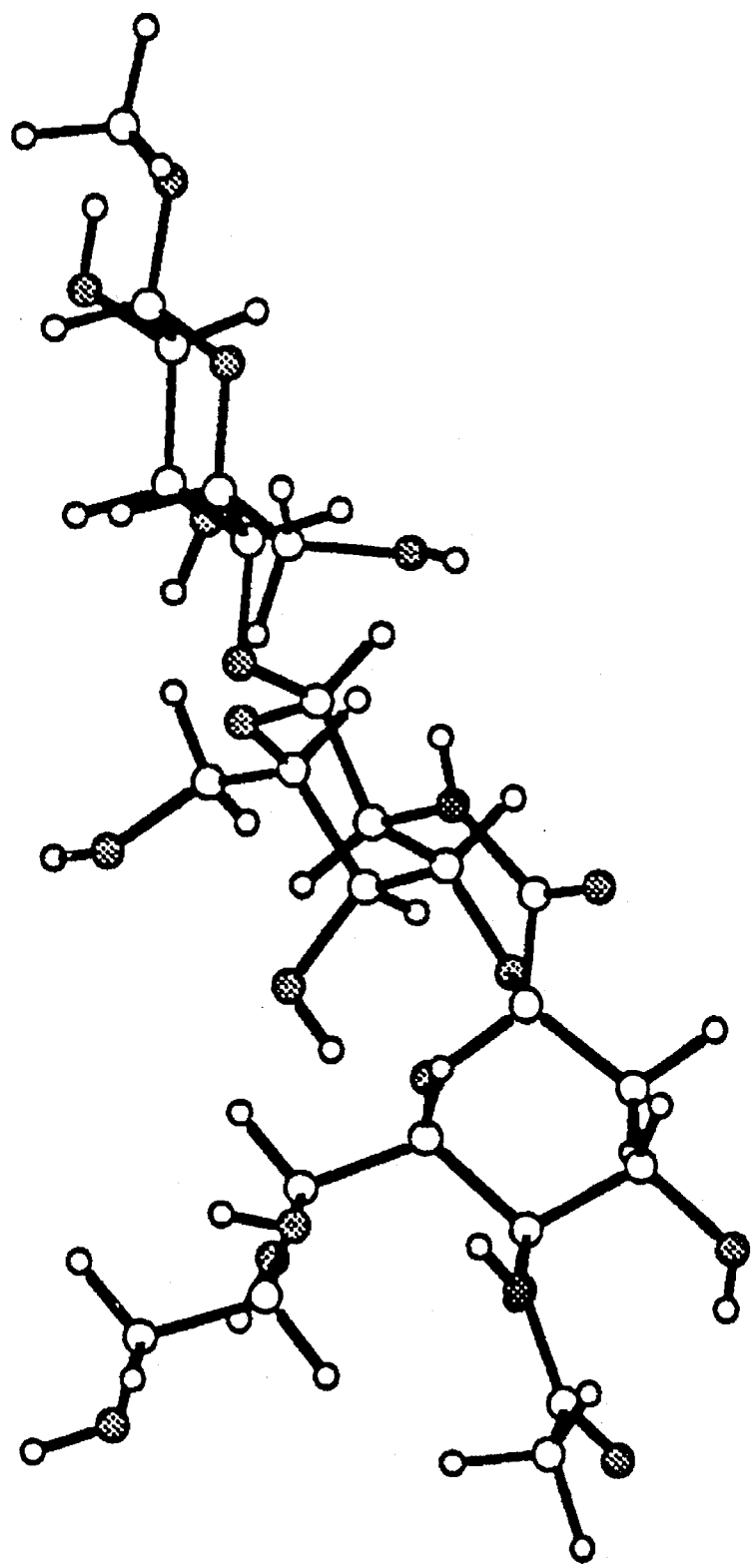
FIG. 1 shows a two-dimensional rendering of the energy-minimized three-dimensional structure of $GM_3$-lactone methyl glycoside.

The invention is further illustrated by the following examples. The various starting materials, intermediates and products 1–29 used or prepared in examples 1–4 are illustrated below.

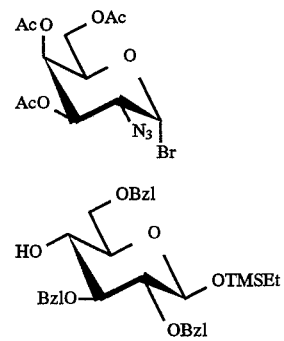

1

2

-continued
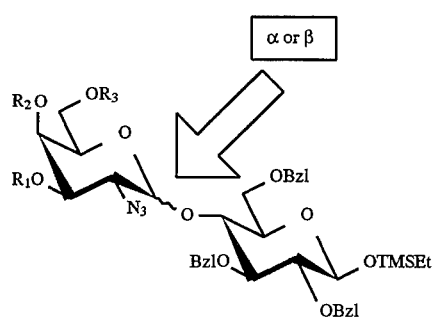
3αβ: $R_1 = R_2 = R_3 = Ac$
4αβ: $R_1 = R_2 = R_3 = H$
5α, 5β: $R_1, R_2 = Me_2C; R_3 = H$
6β: $R_1 = H; R_2, R_3 = Me_2C$
7β: $R_1, R_2 = Me_2C; R_3 = Bzl$
8β: $R_1 = Bzl; R_2, R_3 = Me_2C$
9β: $R_1 = R_2 = H; R_3 = Bzl$
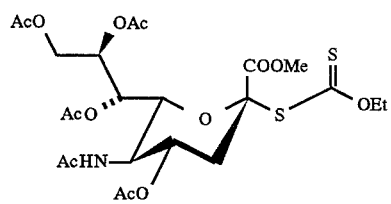 10
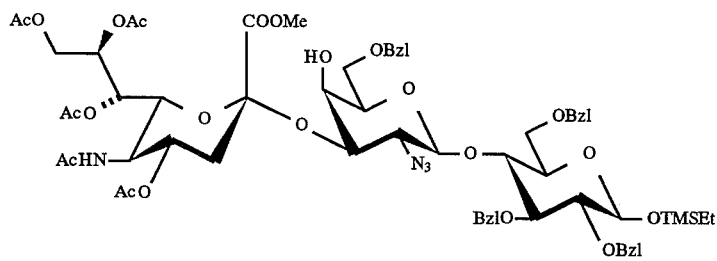 11
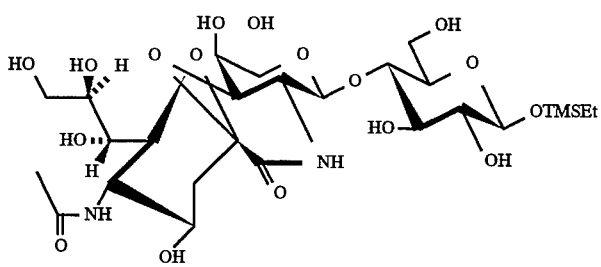 12
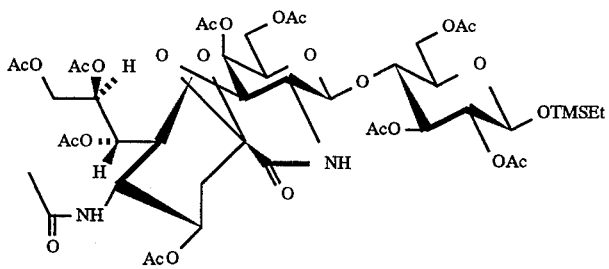 13

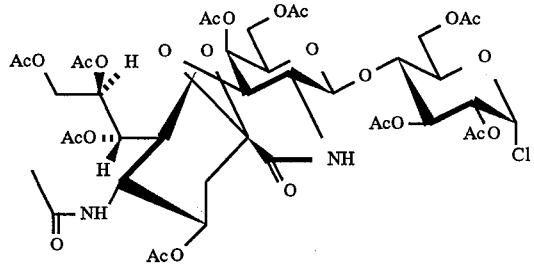 14
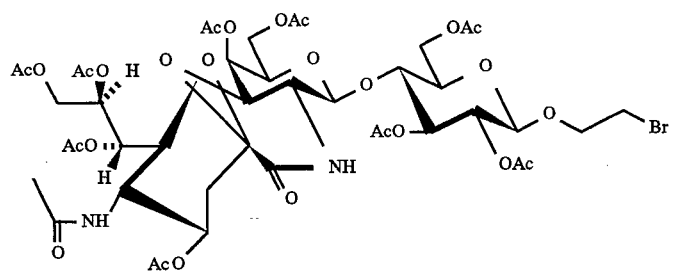 15
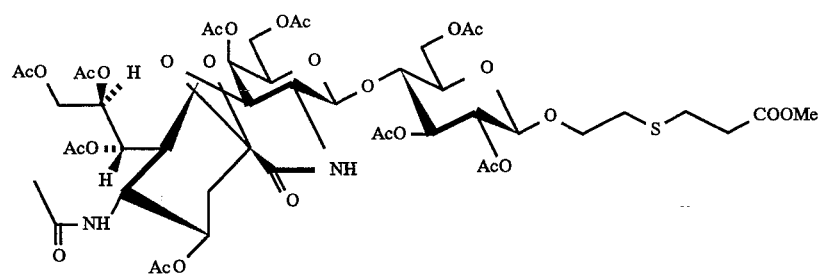 16
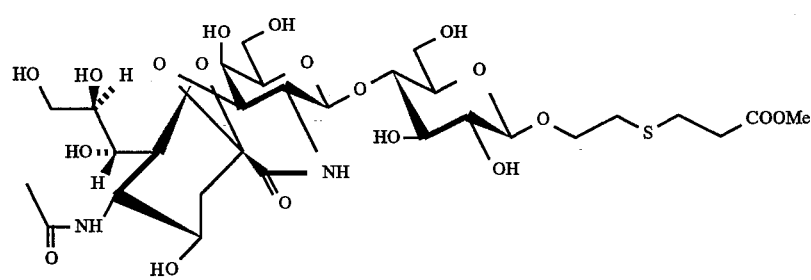 17
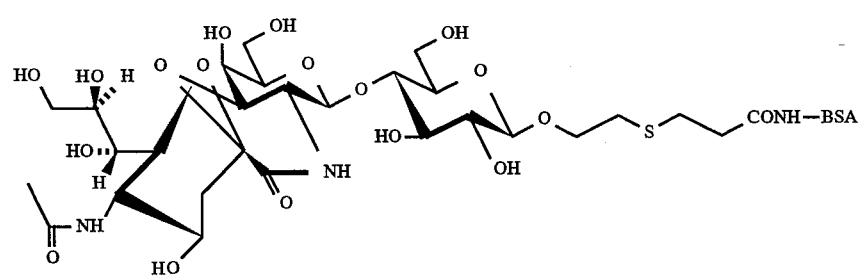 18
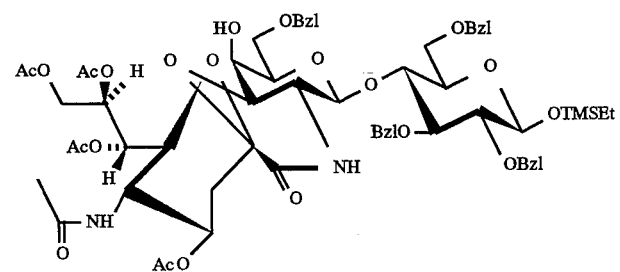 19

-continued
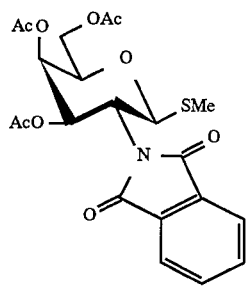
20
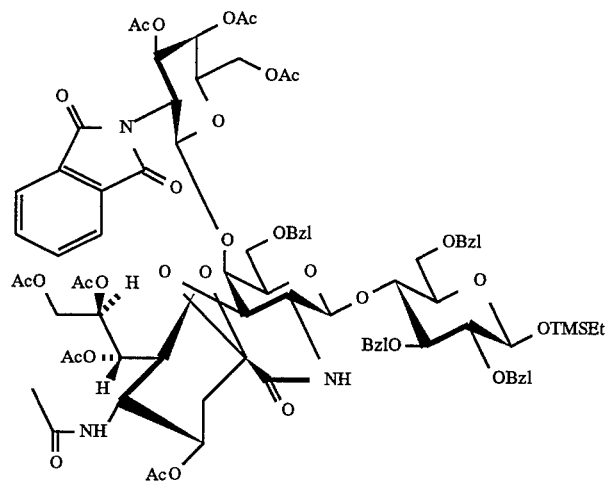
21
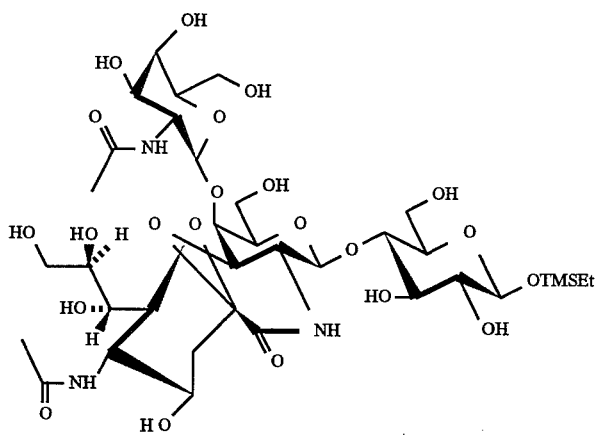
22
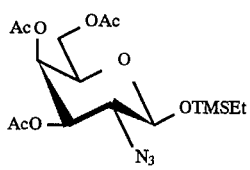
23
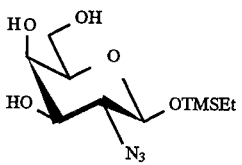
24
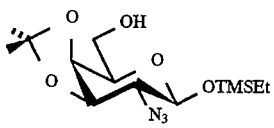
25

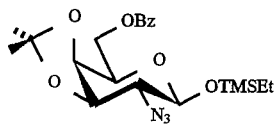

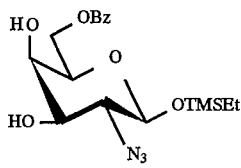

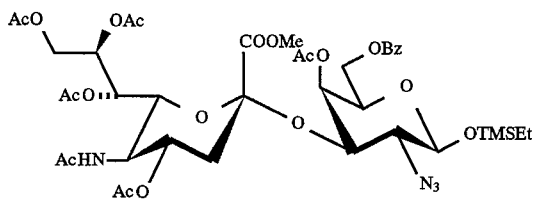

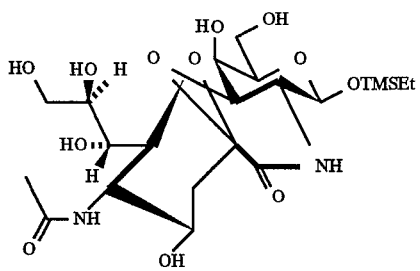

Example 1

Synthesis of the neoglycoprotein GM$_3$-lactam-BSA (18) was performed using the starting materials 1,2, and 10. The intermediates 3–9 and 11–17 were isolated and characterized.

A) 2-(Trimethylsilyl)ethyl 2,3,6-tri-O-benzyl-4-O-(3,4,6-tri-O-acetyl-2-azido-2-deoxy-α/β-D-galactopyranosyl)-β-D-glucopyranoside (3αβ)

Compound 2 (Jansson et al. *J. Org. Chem.* 1988, 53, 5629; 4.5 g, 8.22 mmol), 1 (2.9 g, 7.36 mmol), and dry molecular sieves (4 Å, 3 g) were dissolved in dry dichloromethane (50 mL) and the mixture was stirred under nitrogen for 60 min. Silver silicate (van Boeckel, C. A. A., Beetz, T. *Rec. Trav. Chim. Pays-Bas*, 1987, 106, 596; 8 g) was added and the mixture was stirred vigorously at room temperature for 18 h, then filtered through Celite and concentrated. The residue was chromatographed (SiO$_2$; heptane/EtOAc gradient, 6:1→4:1) to give 3αβ (3.87 g, 61%; α/β ≈8:92).

$^1$H-NMR data (CDCl$_3$) δ 5.19 (d, 1H, J=3.37 Hz, H-4'β), 4.60 (dd, 1H, J=3.27, 10.8 Hz, H-3'β), 4.40 (d, 1H, J=7.6 Hz, H-1β), 4.39 (d, 1H, J=8.1 Hz, H-1'β), 2.09, 2.04, 1.99 (3s, 3H each, OAcβ), 1.05 (m, 2H, CH$_2$Si), 0.04 (s, 9H, SiMe$_3$).

$^{13}$C-NMR (CDCl$_3$) δ 103.3, 103.0, 100.7, 97.6.

B) 2-(Trimethylsilyl)ethyl 2,3,6-tri-O-benzyl-4-O-(2-azido-2-deoxy-α/β-D-galactopyranosyl)-β-D-glucopyranoside (4αβ)

Compound 3αβ (3.7 g, 4.28 mmol) was treated with methanolic sodium methoxide (0.2M, 50 mL) at room temperature for 6 h. The mixture was neutralized with Duolite (H$^+$) resin, filtered and the solvent was removed to give crude 4αβ (3.06 g, 97%), which was used in the next step without purification.

C) 2-(Trimethylsilyl)ethyl 2,3,6-tri-O-benzyl-4-O-(2-azido-2-deoxy-3,4- and -4,6-O-isopropylidene-α/β-D-galactopyranosyl)-β-D-glucopyranoside (5αβ and 6β)

Compound 4αβ (750 mg, 1.01 mmol) and (±)-camphorsulfonic acid (15 mg) were dissolved in 2,2-dimethoxypropane (25 mL) and the mixture was stirred at room temperature for 48 h. Triethylamine (2 mL) was added and the mixture was co-concentrated with toluene (4×20 mL) to remove traces of amine. The residue was dissolved in methanol/water (10:1, 44 mL) and the mixture was refluxed (bath temperature: 85° C.) for 3 hours, then co-concentrated with toluene (3×30 mL). The residue was chromatographed (SiO$_2$; heptane/EtOAc gradient, 5:1→1:2) to give (in order of elution):

5α (61 mg, 8%; R$_f$=0.25, SiO$_2$, heptane/EtOAc 2:1); [α]$_D^{22}$ +71° (c 1.7, CDCl$_3$);

$^1$H-NMR data (CDCl$_3$) δ 5.62 (d, 1H, J=3.7 Hz, H-1'), 4.43 (d, 1H, J=7.8 Hz, H-1), 1.42, 1.29 (2s, 3H each, Me$_2$C), 1.05 (m, 2H, CH$_2$Si), 0.05 (s, 9H, SiMe$_3$), and 5β/6β (19:2; 620 mg, 78%; Rf=0.13, SiO$_2$ heptane/EtOAC, 2:1); [α]$_D^{22}$ +38° (c 1.6, CDCl$_3$);

$^1$H-NMR data for 5β (CDCl$_3$) δ 4.40 (d, 1H, J=7.8 Hz, H-1), 4.21 (d, 1H, J=8.5 Hz, H-1'), 1.55, 1.33 (2s, 3H each, Me$_2$C), 1.04 (m, 2H, CH$_2$Si), 0.04 (s, 9H, SiMe$_3$).

D) 2-(Trimethylsilyl)ethyl 2,3,6-tri-O-benzyl-4-O-(2-azido-6-O-benzyl-2-deoxy-3,4-O-isopropylidene-β-D-galactopyranosyl)-β-D-glucopyranoside (7β) and 2-(Trimethylsilyl) ethyl 2,3,6-tri-O-benzyl-4-O-(2-azido-4-O-benzyl-2-deoxy-4,6-O-isopropylidene-β-D-galactopyranosyl)-β-D-glucopyranoside (8β)

The mixture 5β6β (2.35 g, 3.02 mmol) was dissolved in dimethylformamide (40 mL) and sodium hydride (50% oil coating; 0.3 g, 6.2 mmol) was added with stirring at room temperature. After 1 h, benzyl bromide (0.6 mL, 5 mmol), was added and the mixture was stirred at room temperature over night. Methanol (5 mL) was added dropwise, dichloromethane (300 mL) was added, the mixture was washed with water (5×200 mL), dried (Na$_2$SO$_4$) and concentrated. The residue was chromatographed (SiO$_2$; heptane/EtOAc gradient, 20:1→1:1) to give (in order of elution):

7β (2.24 g, 86%; Rf 0.31, SiO$_2$, heptane/EtOAc 3:1) [α]$_D^{25}$ +21° (c 1.4, CDCl$_3$);

$^1$H-NMR data (CDCl$_3$) δ 4.40 (d, 1H, J=7.8 Hz, H-1), 4.29 (d, 1H, J=8.3 Hz, H-1'), 1.54, 1.36 (2s, 3H each, Me$_2$C), 1.04 (m, CH$_2$Si), 0.04 (s, 9H, SiMe$_3$), and 8β (221 mg, 8%; Rf 0.15, SiO$_2$, heptane/EtOAc 3:1);

$^1$H-NMR data (CDCl$_3$) δ 4.40 (d, 1H, J=7.9 Hz, H-1), 4.26 (d, 1H, J=8.1 Hz, H-1'), 3.10 (dd, 1H, J=3.6, 10.2 Hz, H-3'), 1.45, 1.37 (2s, 3H each, Me$_2$C), 1.04 (m, CH$_2$Si).

E) 2-(Trimethylsilyl)ethyl 2,3,6-tri-O-benzyl-4-O-(2-azido-6-O-benzyl-2-deoxy-β-D-galactopyranosyl)-β-D-glucopyranoside (9β)

Compound 7β (2.20 g, 2.53 mmol), was dissolved in acetic acid/water (50 mL; 85:15) and the mixture was stirred at 85° C. for 90 min., then co-concentrated with toluene (5×20 mL). The residue was chromatographed (SiO$_2$; heptane/EtOAc gradient, 4:1→2:1) to give 9β (1.96 g, 94%); (α)$_D^{22}$ +19° (c 1.1, CDCl$_3$);

$^1$H-NMR data (CDCl$_3$) δ 4.40 (d, 1H, J=7.6 Hz, H-1), 4.31 (d, 1H, J=8.1 Hz, H-1'), 2.76 (d, 1H, J=3.7 Hz, OH), 2.56 (d, 1H, J=8.0 Hz, OH), 1.04 (m, 2H, CH$_2$Si), 0.04 (s, 9H, SiMe$_3$).

F) 2-(Trimethylsilyl)ethyl O-(methyl 5-acetamido-4,7,8,9-tetra-O-acetyl-3,5-di-deoxy-D-glycero-α-D-galacto-2-nonulpyranosylonate)-(2→3)-O-(2-azido-2-deoxy-6-O-benzyl-β-D-galactopyranosyl)-(1→4)-2,3,6-tri-O-benzyl-β-D-glucopyranoside (11)

Compound 9β (1.98 g, 2.39 mmol) and O-ethyl-S-[methyl(5-acetamido-4,7,8,9-tetra-O-acetyl-3,5-di-deoxy-α-D-glycero-D-galacto-2-nonulopyranosyl)onate] (Marra, A. Sinaÿ, P. Carbohydr. Res. 1989, 187, 35; 10; 1.71 g, 2.87 mmol) were dissolved in freshly distilled dry acetonitrile/dichloromethane (70 mL, 3:2) and molecular sieves (3 Å; 4 g, activated by heating) was added. The mixture was stirred under nitrogen at room temperature for 90 min. Silver triflate (0.738 g; 2.87 mmol) was added and the mixture was cooled to −78° C. and stirred for 20 min. Methylsulfenyl bromide (Dasgupta, F., Garegg, P. J. Carbohydr. Res. 1988, 177, c13; 0.365 g, 2.87 mmol) in 1,2-dichloroethane (0.77 mL) was added (syringe) to the reaction mixture and stirring was continued at −78° C. for 2 h. Di-isopropylamine (1 mL) was added and the mixture was stirred at −78° C. for 1 h, then filtered through Celite with dichloromethane (300 mL, ~20° C.). The mixture was washed with saturated aqueous sodium hydrogen carbonate and water, dried (Na$_2$SO$_4$) and concentrated. The residue was chromatographed (SiO$_2$; toluene/EtOH gradient, 45:1→25:1) to give impure 11. A second chromatography (SiO$_2$) using different solvents gave the following compounds:

i) with hexane/EtOAc (1:1), 9β (0.81 g, 41%);
ii) with toluene/EtOAc (5:4→1:1→1:2), 2"-3'-β-linked trisaccharide (0.15 g, 5%);
iii) with toluene/EtOAc (1:3), compound 11 (1.63 g, 52%);
iv) with EtOAc, the 2,3-elimination product of 10 (0.59 g, 43%).

Compound 11 had: [α]$_D^{22}$ −13° (c 1.1, CDCl$_3$);

$^1$H-NMR data (CDCl$_3$) δ 5.54 (m, 1H, H-8"), 5.32 (bd, 1H, H-7"), 5.19 (bd, 1H, NH), 4.50 (d, 1H, J=8.2 Hz, H-1'), 4.40 (d, 1H, J=7.3 Hz, H-1), 4.17 (dd, 1H, J=3.2, 10.0 Hz, H-3'), 3.75 (s, 3H, COOMe), 2.67 (dd, 1H, J=4.4, 12.9 Hz, H-3"eq), 2.10, 2.06, 2.05, 1.98, 1.89, (5s, 3H each, OAc, NHAc), 1.04 (m, 2H CH$_2$Si), 0.03 (s, 9H, SiMe$_3$);

$^{13}$C-NMR data (CDCl$_3$) δ 170.9, 170.6, 170.2, 170.1, 170.0, 168.4, 139.3, 138.7, 138.5, 138.1, 128.3, 128.2, 128.1, 127.6, 127.5, 127.46, 127.4, 127.1, 103.1, 100.6, 97.5, 83.1, 82.1, 76.9, 75.2, 74.9, 74.8, 73.3, 73.2, 72.5, 72.2, 69.0, 68.7, 68.4, 68.3, 674, 67.1, 66.9, 62.7, 62.4, 53.1, 49.3, 37.0, 23.2, 21.2, 20.9, 20.7, 20.6, 18.5, −1.4.

G) TMSEt GM$_3$-lactam (12)

Compound 11 (400 mg,0.306 mmol), nickel chloride (NiCl$_2$/6 H$_2$O; 1.37 g, 5.75 mmol), and boric acid (648 mg, 11.1 mmol) were dissolved in ethanol (30 mL) and the mixture was stirred and cooled to 0° C. A solution of sodium borohydride (308 mg, 8.14 mmol) in ethanol (20 mL) was added dropwise during 10 min. After 10 min., the mixture was concentrated and the residue was dissolved in dichloromethane (50 mL). The mixture was washed with saturated aqueous sodium hydrogen carbonate and water, dried (Na$_2$SO$_4$) and concentrated. The residue was treated with methanolic sodium methoxide (0.05M, 5 mL) at room temperature over night, then neutralized with acetic acid and co-concentrated with toluene. The residue was stirred with pyridine (5 mL) at room temperature over night and co-concentrated with toluene. The residue was filtered through silica (CHCl$_3$/MeOH 10:1) and the filtrate was concentrated. The residue was hydrogenolyzed (H$_2$, Pd/C., 10%, 1 atm.) in acetic acid (10 mL) at room temperature over night. The mixture was filtered through Celite and the filtrate was concentrated. The residue was chromatographed (SiO$_2$; CHCl$_3$/MeOH/H$_2$O gradient, 10:4:1→→10:6:1) to give 12 (118 mg, 54%); [α]$_D^{24}$ −22° (c 0.7, MeOH);

$^1$H-NMR data (D$_2$O) δ 4.69 (d, 1H, J=8.0 Hz, H-1'), 4.47 (d, 1H, J=8.1 Hz, H-1), 4.32 (m, 1H, H-4"), 3.23 (t, 1H, J=9.0 Hz, H-2), 2.59 (dd, 1H, J=5.3, 13.4 Hz, H-3"eq), 2.02 (s, 3H, NHAc), 1.67 (dd, 1H, J=11.4, 12.9 Hz, H-3"ax), 1.00 (m, 2H, CH$_2$Si), 0.00 (s, 9H, SiMe$_3$);

13C-NMR (D$_2$O) δ 175.9, 169.6, 102.3, 100.7, 98.8, 78.9, 78.8, 77.0, 74.9, 74.8, 73.9, 73.2, 71.0, 69.3, 68.6, 67.5, 66.3, 64.1, 61.8, 61.5, 52.6, 51.6, 40.1, 22.9, 18.4, −1.7.

H) TMSEt GM$_3$-lactam-Ac (13)

Compound 12 (113 mg, 0.158 mmol) was treated with acetic anhydride/pyridine (1:1,5 mL) at room temperature for 24 h, then co-concentrated with toluene. The residue was chromatographed (SiO$_2$; toluene/ethanol, 5:1) to give 13 (170 mg, 98%); [α]$_D^{24}$ −32° (c 0.8, CDCl$_3$);

$^1$H-NMR data (CDCl$_3$) δ 5.61 (bd, 1H, J=10.5 Hz, H-7"), 5.46 (bdt, 1H, H-4"), 4.45 (dd, 1H, J=7.9, 9.2 Hz, H-2), 4.54 (d, 1H, J=7.8 Hz, H-1), 4.40 (d, 1H, J=8.6 Hz, H-1'), 2.40 (dd, 1H, J=5.6 and 13.4 Hz, H-3"eq), 2.20, 2.18, 2.09, 2.09, 2.08, 2.06, 2.04, 2.03, 2.00, 1.89 (9s, 3H each, OAc, NHAc), 1.79 (dd, 1H, J=11.4, 12.9 Hz, H-3"ax), 0.90 (m, 2H, CH$_2$Si), 0.00 (s, 9H, SiMe$_3$).

I) Chloro GM$_3$-lactam-Ac (14)

Compound 13 (167 mg, 0.153 mmol) and dichloromethylmethyl ether (0.105 mL, 1.18 mmol) were dissolved in dry chloroform (4 mL) and freshly fused zinc chloride (≈20 mg) was added. The mixture was stirred at room temperature over night, chloroform (25 mL) was added, the mixture was washed with saturated aqueous sodium hydrogen carbonate and water, dried (Na$_2$SO$_4$) and concentrated to give crude 14, which was used without purification.

$^1$H-NMR data (CDCl$_3$) δ 6.20 (d, 1H, J=3.9 Hz, H-1).

J) 2-Bromoethyl GM$_3$-lactam-Ac (15)

Compound 14 (156 mg, 0.154 mmol) was added dropwise to a stirred mixture of 2-bromoethanol (0.1 mL; 1.4 mmol), silver trifluoromethane sulfonate (52 mg, 0.2 mmol), and molecular sieve (3 Å, 0.1 g) in dichloromethane (2 mL) at −28° C. under nitrogen. After 4 h, the cooling bath was removed and the mixture was left over night, then filtered through Celite, washed with saturated aqueous sodium hydrogen carbonate and water, dried ($Na_2SO_4$), and concentrated. The residue was chromatographed ($SiO_2$; toluene/ethanol, 10:1) to give 15 (90 mg, 54%) as an α,β-mixture (15:85);

$[\alpha]_D^{25}$ −27° (c 1.2, $CDCl_3$);

$^1$H-NMR data ($CDCl_3$) δ 4.90 (dd, 1H, J=8.0, 9.4 Hz, H-2), 4.78 (d, 1H, J=8.1 Hz, H-l), 3.42 (bt, 2H, $OCH_2CH_2$), 2.40 (dd, 1H, J=5.6, 13.2 Hz, H-3"eq), 2.20, 2.15, 2.13, 2.07, 2.06, 2.05, 2.00, 1.89, (8s, 30H, OAc, NHAc).

K) Spacer-$GM_3$-lactam-Ac (16)

Compound 15 (90 mg, 0.082 mmol), cesium carbonate (32 mg, 0.10 mmol), and dimethylformamide (4.5 mL) were stirred at room temperature under nitrogen for 10 min. Methyl 3-mercaptopropionate (37 μL, 0.33 mmol) was added, the mixture was stirred for 2.5 h, dichloromethane (30 mL) was added, and the mixture was washed with water, dried ($Na_2SO_4$) and concentrated. The residue was chromatographed ($SiO_2$; toluene/ethanol gradient, 15:1→10:1) to give 16 (77 mg, 82%) as an α,β-mixture (~15:85); $[\alpha]_D^{22}$ −23° (c 1.1, $CDCl_3$);

$^1$H-NMR data ($CDCl_3$) δ 4.88 (dd, 1H, J=8.0, 9.5 Hz, H-2), 4.63 (d, 1H, J=7.9 Hz, H-l), 3.69 (s, 3H, COOMe), 2.78, 2.68, 2.60 (t, 2H each, $CH_2$), 2.38 (bdd, 1H, H-3"eq), 2.19, 2.15, 2.11, 2.07, 2.068, 2.06, 2.04, 2.00, 1.99, 1.89, (10s, 3H each, OAc, NHAc);

$^{13}$C-NMR ($CDCl_3$) δ 172.171.4, 171.2, 170.8, 170.4, 170.3, 170.1, 169.9, 169.8, 169.7, 167.7, 100.5, 100.2, 97.8, 77.2, 76.7, 75.2, 75.1, 73.0, 72.3, 72.1, 71.7, 71.4, 70.4, 69.7, 69.4, 67.3, 65.1, 62.6, 61.0, 51.8, 50.9, 48.7, 37.3, 34.7, 31.5, 29.7, 27.4, 23.1, 21.1, 21.0, 21.0, 20.8, 20.7, 20.67, 20.6, 20.5, 14.6.

L) Spacer-$GM_3$-lactam (17)

Compound 16 (49 mg, 0.043 mmol) was dissolved in methanolic sodium methoxide (0.02M, 2 mL) and the mixture was stirred at room temperature for 4 h, then neutralized with Duolite $H^+$ resin, filtered and concentrated. The residue was chromatographed ($SiO_2$; $CHCl_3$/MeOH/$H_2O$, 10:5:1) to give 17 (28 mg, 86%) as an α,β-mixture (~1:8); $[\alpha]_D^{24}$ 0.1° (c 0.5, MeOH);

$^1$H-NMR data ($CDCl_3$) δ 4.92 (d, 1H, J=4.1 Hz, H-1α), 4.69 (d, 1H, J=8.1 Hz, H-1'), 4.48 (d, 1H, J=8.1 Hz, H-1β), 4.32 (m, 1H, H-4"), 3.70 (s, 3H, COOMe), 3.30 (t, 1H, J=8.1 Hz, H-2), 2.85, 2.81 (bt, 2H each, $CH_2$), 2.71 (bt, 2H, $CH_2$), 2.57 (dd, 1H, J=5.4, 13.2 Hz, H-3"eq), 2.02 (s, 3H, NHAc), 1.67 (dd, 1H, J=10.3, 13.2 Hz, H-3"ax);

$^{13}$C-NMR data ($D_2O$) δ 175.9, 169.6, 103.1, 100.7, 98.8, 78.74, 78.71, 77.0, 75.0, 74.6, 73.8, 73.2, 71.0, 69.9, 68.6, 66.2, 64.1, 61.8, 61.5, 53.1, 52.6, 51.6, 40.1, 35.0, 31.6, 27.3, 22.9, 13.0, 12.9.

M) $GM_3$-lactam-BSA-conjugate (18)

Compound 17 (22 mg, 28.9 μmol), and hydrazine hydrate (85%, 0.25 mL) were dissolved in ethanol (2 mL) and the mixture was stirred at room temperature over night and concentrated. The residue was dissolved in water and freeze-dried. The resulting hydrazide was dissolved in dimethylsulfoxide (0.5 mL) and hydrogen chloride in dioxane (4M, 53 μL) was added followed by a solution of tert. butylnitrite (9 μL, 75 μmol) in dimethylsulfoxide (50 μL). The mixture was stirred at room temperature for 30 min. and a solution of sulfamic acid (5 mg, 55 μmol) in dimethylsulfoxide (50 μL) was added. After 15 min. the mixture was added dropwise with stirring to a solution of bovine serum albumin (27 mg, 0.41 μmol) in sodium tetraborate-potassium hydrogen-carbonate buffer (1 mL, 0.08M $Na_2B_4O_7$ and 0.35M $KHO_3$). The pH was maintained at 8.5–9.5 by addition of sodium hydroxide solution (1M). The mixture was stirred at 4°–15° C. for 1 h and at room temperature over night, then dialyzed against distilled water for 4 d and freeze dried to give 18 (33 mg). The degree of binding (mol of 18 per mol of BSA) was 21 according to sulfur combustion analysis.

Example 2

Preparation of TMSEt $GM_2$-lactam (22)

A) Compound 19

Compound 11 (1 g, 0.768 mmol) in ethanol (60 ml) was cooled to ~0° C. $NiCl_2$,$6H_2O$ (3.42 g, 14.4 mmol) and $H_3BO_3$ (1.72 g, 27.8 mmol) in ethanol (60 ml) was added dropwise during 15 min. with stirring. Stirring and cooling were continued for another 15 min. The reaction mixture was concentrated to dryness, dissolved in $CH_2Cl_2$ (~150 ml) and washed with a saturated solution of $NaHCO_3$ and water, respectively. The organic layer was dried ($Na_2SO_4$) and evaporated to dryness. The residue was taken up in pyridine (20 ml) and stirred at 85° C. for 48 hours. Evaporation and co-evaporation with toluene (10 ml×3) followed by chromatography (toluene-EtOAc 1:2) gave pure 19 (677 mg, 70.8%) as an amorphous powder having $[\alpha]_D^{22}$ −5° (c 1.1, $CHCl_3$).

$^1$H-NMR ($CDCl_3$) δ 5.63 (m, 1H, H-4"), 5.33 (d, 1H, J=10.2 Hz, AcNH), 5.27 (dd, 1H, J=2.20, 5.86 Hz, H-7), 5.16 (m, 1H, H-8"), 4.48 (d, 1H, J=8.05 Hz, H-1), 4.37 (d, 1H, J=8.30 Hz, H-1), 2.67 (d, 1H, J=2.2 Hz, OH), 2.49 (dd, 1H, J=5.64, 13.3 Hz, H-3"eq), 2.16, 2.03, 2.02, 1.96, 1.88 (5s, 4OAc and NHAc), 1.85 (dd, 1H, J=11.3, 12.9 Hz, H-3"ax), 1.26 (m, 2H, $CH_2Si$), 0.05 (s, 9H, $SiMe_3$).

B) Methyl 3,4,6-tri-O-acetyl-2-deoxy-2-phthalimido-1-thio-β-D-galactopyranoside (20)

A mixture of 1,3,4,6-tetra-O-acetyl-2-deoxy-2-phthalimido-β-D-galactose (680 mg, 1.425 mmol), methylthiotrimethylsilane (0.8 ml, 5.64 mmol), and trimethyl silyl triflate (0.32 ml, 1.66 mmol) in $CH_2Cl_2$ was stirred at room temperature for 2 days. Diisopropylamine (~1 ml) was added, diluted with $CH_2Cl_2$ (~50 ml) and washed with saturated $NaHCO_3$ solution and water, respectively. The organic layer was dried ($Na_2SO_4$) and evaporated to dryness. Column chromatography (heptane-EtOAc) gave pure 20 (630 mg, 95%) as an amorphous powder, having $[\alpha]_D^{24}$ +25° (c1, $CHCl_3$).

$^1$H-NMR data ($CDCl_3$) δ 7.87–7.74 (m, 4H, aromatic), 5.87 (dd, 1H, J=3.4, 11.0 Hz, H-3), 5.52 (d, 1H, J=3.2 Hz, H-4), 5.35 (d, 1H, J=10.6 Hz, H-1), 4.63 (t, 1H, J=10.8 Hz, H-2), 4.25–4.10 (m, 3H, H-6, H-5), 2.20 (s, 3H, $SCH_3$), 2.19, 2–05, 1.85 (3s, 9H, 3 OAc).

C) Compound 21

Compound 19 (200 mg, 0,161 mmol), 20 (150 mg, 0.322 mmol) and molecular sieves 3 Å (0.1 g) in $CH_2Cl_2$—$CH_3CN$ (2:1, 3 ml) was stirred under $N_2$ for 1 h. Silver triflate (0,084 g, 0.327 mmol) was added, flashed with $N_2$, cooled to −78° C. Methylsulfenyl bromide (0.041 g, 0,322 mmol, in 1,2-dichloroethane 0.09 ml) was injected in 4 portions. The temperature was raised to −28° C. and the mixture was stirred for 3 h. Diisopropyl amine (0.2 ml) was added and stirred for 30 min. The mixture was filtered through celite, diluted with $CH_2Cl_2$ (50 ml), and washed with saturated $NaHCO_3$ solution and water respectively. The organic layer was dried ($Na_2$–$SO_4$) and evaporated to dryness. Column chromatography (toluene-EtOH 40:1→30:1) gave 21 (137 mg; 51%) as a powder, having $[\alpha]_D^{22}$ −18° (c 0.7, $CHCl_3$).

$^1$H-NMR data ($CDCl_3$) δ 7.8–7.2 (m, aromatic), 5.81 (d, 1H, J=8.4 Hz, H-1'''), 5.53 (dd, 1H, J=3.2, 12.4 Hz, H-3'''), 5.41 (m, 1H, H-4"), 5.36 (bd, J=2.7 Hz, H-4'''), 5.31 (m, 2H, H-7'', 8'''), 5.19 (d, 1H, J=10.3 Hz, NH), 4.56 (dd, 1H, J=8.4, 11.5 Hz, H-2'''), 3.07 (dd, 1H, J=5.7, 9.1 Hz, H-3''eq), 2.18–1.81 (7s, 24H, 7 OAc and NHAc), 1.00 (m, 2H, CH$_2$Si), 0.02 (s, 9H, SiMe$_3$).

D) TMSEt GM$_2$-lactam (22)

Compound 21 (90 mg, 0.054 mmol) and 10% Pd-C(50 mg) in glacial acetic acid (3 ml) was stirred under hydrogen overnight at room temperature, filtered through celite and evaporated. The residue was taken up in ethanol (3 ml), hydrazine hydrate (0.3 ml) was added and stirred at 85 C. for 1 h 20 min. after which it was diluted to 20 ml (ethanol), evaporated and co-evaporated with ethanol (5×10 ml). The residue was stirred in pyridine/Ac$_2$O ) (1:1, 3 ml) for 1 hour at room temperature and then evaporated and co-evaporated with toluene (5×5 ml). Deacetylation was done with methanolic NaOMe (0.05M, 2 ml) for 2 hours at room temperature. The mixture was then decationised with Duolite H$^+$ resin, filtered, and evaporated. Column chromatography (CHCl$_3$-MeOH-H$_2$O, 10:5:1) of the residue gave 22 (24 mg, 48.2%) having $[\alpha]_D^{22}$ −29° (c 0.8, MeOH).

$^1$H-NMR data (D$_2$O) δ 4.68 (d, 1H, J=8.41 Hz, H-1'), 4.62 (d, 1H, J=8.1 Hz, H-1'''), 4.47 (d, 1H, J=8.05 Hz, H-1), 4.36–4.26 (m, 2H, H-4''', H-5''), 3.55 (bd, 1H, J=9.8 Hz, H-7''), 3.42 (dd, 1H, J=8.2, 10.1 Hz, H-2'''), 3.25 (t, 1H, J=8.5 Hz, H-2), 2.63 (dd, 1H, J=5.95, 14.9 Hz, H-3''eq), 2.12 (dd, 1H, J=5.13, 14.9 Hz, H-3''ax), 2.03, 2.02 (2s, 6H, 2NHAc), 0.99 (m, 2H, CH$_2$Si), 0.00 (s, 3H, SiMe$_3$).

Example 3

Preparation of TMSEt GM$_4$-lactam (29)

A) 2-(Trimethylsilyl)ethyl 3,4,6-tri-O-acetyl-2-azido-2-deoxy-β-D-galactopyranoside (23)

3,4,6-Tri-O-acetyl-2-azido-2-deoxy-α-D-galactopyranosyl bromide (6 g, 15.2 mmol), 2-(trimethylsilyl)-ethanol (2.7 g, 22.8 mmol) and powdered molecular sieves 4 Å (14.6 g) in dry CH$_2$Cl$_2$ (100 ml) was stirred under N$_2$ for 1 h. Silver silicate (369) was added. After 20 min. stirring, the reaction mixture was filtered through celite and the filtrate was evaporated to dryness. Column chromatography (heptane-EtOAc 3:1) of the residue gave 23 (5.11 g, 78%) as a syrup. $[\alpha]_D^{25}$ −18° (c 1, CHCl$_3$).

$^1$H-NMR data (CDCl$_3$) δ 5.32 (bd, 1H, H-4), 4.77 (dd, 1H, J=3.3, 10.9 Hz, H-3), 4.37 (d, 1H, J=8.0 Hz, H-1), 4.22–3.98 (m, 3H, H-6, OCH$_2$), 3.85 (m, 1H, H-5), 3.70–3.61 (m, 2H, H-2, OCH$_2$), 2.15–2.04 (3s, 9H, 3OAc), 1.06 (m, 2H, CH$_2$Si), 0.04 (s, 9H, SiMe$_3$).

B) 2-(Trimethylsilyl)ethyl 2-azido-2-deoxy-β-D-galactopyranoside (24)

Compound 23 (4.88 g, 11.3 mmol) was stirred in methanolic NaOMe (0.04M, 50 ml) for 90 min. The mixture was decationised with Amberlite IR-120(H$^+$) resin, filtered and evaporated to dryness to give 24 (3.24 g, 94%), $[\alpha]_D^{25}$ +8.5° (c 0.8, MeOH), m.p. 158°–161° C. (ether-heptane).

$^1$H-NMR data (CD$_3$OD) δ 4.29–4.26 (m, 1H, H-1), 4.10–4.01 (m, 1H, OCH$_2$), 3.99 (dd, 1H, 1.1, 2.6 Hz, H-4), 3.73 (m, 2H, H-2,3), 3.65 (m, 1H, OCH$_2$), 3.46 (m, 1H, H-5), 3.43 (m, 2H, H-6), 1.00 (m, 2H, CH$_2$Si), 0.05 (S, 9H, SiMe$_3$).

c) 2-(Trimethylsilyl)ethyl 2-azido-2-deoxy-3,4-isopropylidene-β-D-galactopyranoside (25)

Compound 24 (1.0 g, 3.27 mmol) in 2,2-dimethoxypropane (15 ml) was stirred in the presence of a catalytic amount (~10 mg) of p-toluenesulfonic acid for 24 h. Triethylamine (~0.5 ml) was added and the mixture was evaporated to dryness and co-evaporated with toluene (2×10 ml) to remove traces of Et$_3$N. The residue was refluxed in 80% methanol for 5 h, then concentrated. Column chromatography (heptane-EtOAC, 2:1 containing 0.1% Et$_3$N) gave 25 (0.98 g, 86%), $[\alpha]_D^{25}$ +40.4° (c 0.9, CHCl$_3$), m.p. 82°–83° C. (heptane).

$^1$H-NMR data (CDCl$_3$) δ 4.24 (d, 1H, J=8.51 Hz, H-1), 4.10 (dd, 1H, J=2.0, 5.4 Hz, H-4) 4.04-3-81 (m, 6H), 3.62 (m, 1H, OCH$_2$CH$_2$), 3.38 (t, 1H, H-2), 2.07 (dd, 1H, OH), 1.54, 1.34 (2s, 6H, CMe$_2$), 1.05 (m, 2H, CH$_2$Si), 0.04 (s, 9H, SiMe$_3$).

D) 2-(Trimethylsilyl)ethyl 2-azido-2-O-benzoyl-2-deoxy-3,4-isopropylidene-β-D-galactopyranoside (26)

Benzoyl chloride (0.4 g, 3.29 mmol) was added to a solution of 25 (0.87 g, 2.53 mmol) in pyridine (10 ml) at 0° C. After 1 h, water (0.5 ml) was added. The mixture was diluted with CH$_2$Cl$_2$ (50 ml) and washed with saturated NaHCO$_3$ solution and water respectively. The organic layer was dried (Na$_2$SO$_4$) and evaporated. Column chromatography of the residue (heptane-EtOAc) gave 26 (1.12 g, 98%) as a syrup, $[\alpha]_D^{25}$+61° (c 0.9, CHCl$_3$).

$^1$H-NMR data (CDCl$_3$) δ 8.06–7.57 (m, 5H, aromatic), 4.25 (d, 1H, J=8.5 Hz, H-1), 4,17 (dd, 1H, J=2.2, 5.3 Hz, H-4), 3.42 (t, 1H, H-2), 1.57, 1.36 (2s, 6H, CMe$_2$), 1.04 (m, 2H, CH$_2$Si), −0.01 (s, 9H, SiMe$_3$).

E) 2-(Trimethylsilyl)ethyl 2-azido-6-O-benzoyl-2-deoxy-β-D-galactopyranoside (27)

Compound 26 (1.07 g, 2.37 mmol) is 80% aqueous acetic acid (15 ml) was stirred at 90° C. for 2 h. The mixture was concentrated and the residue was chromatographed (heptane-EtOAc 2:1) to give 27 (0.8 g, 83%), m.p. 55°–57° C. (ether-heptane), $[\alpha]_D^{25}$ 37.8° (c 1, CHCl$_3$).

$^1$H-NMR data (CDCl$_3$) δ (8.03–7.45 ml, 5H, aromatic), 4.69 (dd, 1H, J=6.9, 11.4 Hz, H-6), 4.50 (dd, 1H, J=6.5, 11.4 Hz, H-6), 4.32 (d, 1H, J=7.6 Hz, H-1), 4.00 (m, 1H, OCH$_2$CH$_2$), 3.92 (bd, 1H, H-4), 3.77 (m, 1H, H-5), 3.63 (m, 1H, OCH$_2$CH$_2$), 3.54 (m, 1H, H-29, 3.42 (dd, 1H, J=3.3, 10.0 Hz, H-3), 1.05 (m, 2H, CH$_2$Si), 0.00 (s, 9H, SiMe$_3$).

F) 2-(Trimethylsilyl)ethyl O-(methyl 5-acetamido-4,7,8,9-tetra-O-acetyl-3,5-dideoxy-D-glycero-α-D-galacto-2-nonulpyranosylonate)-(2→3)-O-4-O-acetyl-2-azido-2-deoxy-6-O-benzoyl-β-D-galactopyranoside (28)

Compound 27 (0.5 g, 1.22 mmol), 10 (0.9 g, 1.51 mmol) and powdered molecular sieves (3 Å, 1.5 g,) in CH$_2$Cl$_2$—CH$_3$CN (2:3, 40 ml) was stirred under N$_2$ at room temperature for 1 h. Silver triflate (0.41 g, 1.61 mmol) was added and the mixture was cooled to −78° C. Methylsulfenyl bromide (0.19 g, 1.47 mmol) in 1,2-dichloroethane (0.37 ml) was added in 3 portions stirring was continued at −78° C. for 3 hours 30 min. Diisopropylamine (0.27 ml) was added and stirred for 30 min. at −78° C. After usual work-up (see work up procedure for preparation of compound 11), the residue was chromatographed (MTBE-EtOH 20:1) to give a mixture which was acetylated (pyridine/Ac$_2$O 1:1, 20 ml, 2 h). Solvents were removed and the residue was chromatographed (EtOAc-toluene 1:1→8:1) to give 28 (661 mg, 58%) as a powder, $[\alpha]_D^{25}$ −45° (c 1, CHCl$_3$).

$^1$H-NMR data (CDCl$_3$) δ 8.02–7.42 (m, 5H, aromatic), 5.61 (m, 1H, H-8'), 5.25 (dd, 1H, J=1.9, 9.3 Hz, H-7'), 5.06 (d, 1H, J=9.96 Hz, NHAc), 4.99 (m, 2H, H-4, H-4'), 4.62 (dd, 1H, J=3.4, 10.1 Hz, H-3), 4.41 (m, 1H, H-6a), 4.37 (d, 1H, J=8.1 Hz, H-1), 4.31 (dd, 1H, J=2.5, 12.7 Hz, H-9'a), 4.24 (dd, 1H, J=6.2, 11.3 Hz, H-6b), 4.10 (dd, 1H, J=4.8, 12.7 Hz, H-9'b), 3.99 (m, 3H), 3.80 (s, 3H, OCH$_3$), 3.62 (m, 2H), 2.64 (dd, 1H, J=4.6, 12.5 Hz, H-3'eq), 2.13–2.04 (5s, 15 H, 5 OAc), 1.94 (m, 1H, H-3'ax), 1.88 (s, 3H, NHAc), 1.08 (m, 2H, CH$_2$Si), 0.00 (s, 9H, SiMe$_3$).

G) TMSEt GM₄-lactam (29)

NaBH₄ (204 mg, 5.4 mmol) in ethanol (12 ml) was added dropwise to a stirred solution of compound 28 (50 mg, 0.0534 mmol), NiCl₂, 6H₂O (400 mg, 1.68 mmol), H₃BO₃ (120 mg, 1.0 mmol) in ethanol (5 ml) at 0° C. during 4 h. The mixture was then evaporated and the residue was taken up in CH₂Cl₂ (60 ml) and washed with saturated solution of NaHCO₃ and water, respectively. The organic layer was dried (Na₂-SO₄) and evaporated. The residue was stirred in methanolic NaOMe (0.05M, 5 ml) for 2 h neutralised with AcOH and evaporated. The residue was filtered through SiO₂ (CH₂Cl₂-MeOH 1:1/(CH₂Cl₂-MeOH 1:1). The filtrate was evaporated and stirred with pyridine (2 ml), triethylamine (2 ml) and 4-dimethylaminopyridine (6 mg) for 2 days at room temperature. The solvents were removed by evaporation and the residue was chromatographed (CH₂Cl₂-MeOH 6:1) to give 29 (18 mg; 61%) as a white powder. $[\alpha]_D^{25}$ -13.4° (c 1, H₂O).

¹H-NMR data (D₂O) δ 4.57 (d, 1H, J=8.2 Hz, H-1), 4.32 (m, 1H, H-4'), 4.06 (m, 1H, OCH₂CH₂), 4.02 (bd, 1H, H-4), 3.96 (dd, 1H, J=2.6, 10:7 Hz, H-3), 3.87 (t, 1H, J=10.3 Hz, H-5), 2.55 (dd, 1H, J=5.4, 10.2 Hz, H-3'eq), 2.01 (s, 3H, NHAC), 1.66 (dd, 1H, J=11.5, 12.9 Hz, H-3'ax), 1.02 (m, 2H, CA₂Si), 0.00 (s, 9H, SiMe₃).

Example 4

Conformational Studies

Initially, studies were made of the conformational structure of GM₃-lactone, i.e. the lactone of the naturally occurring GM₃ganglioside. It was surprisingly found that in contrast to the structure suggested by Yu et al. cited above, GM₃-lactone is better described by two structures where the lactone ring is present as boat-like conformations (see Scheme 1 below).

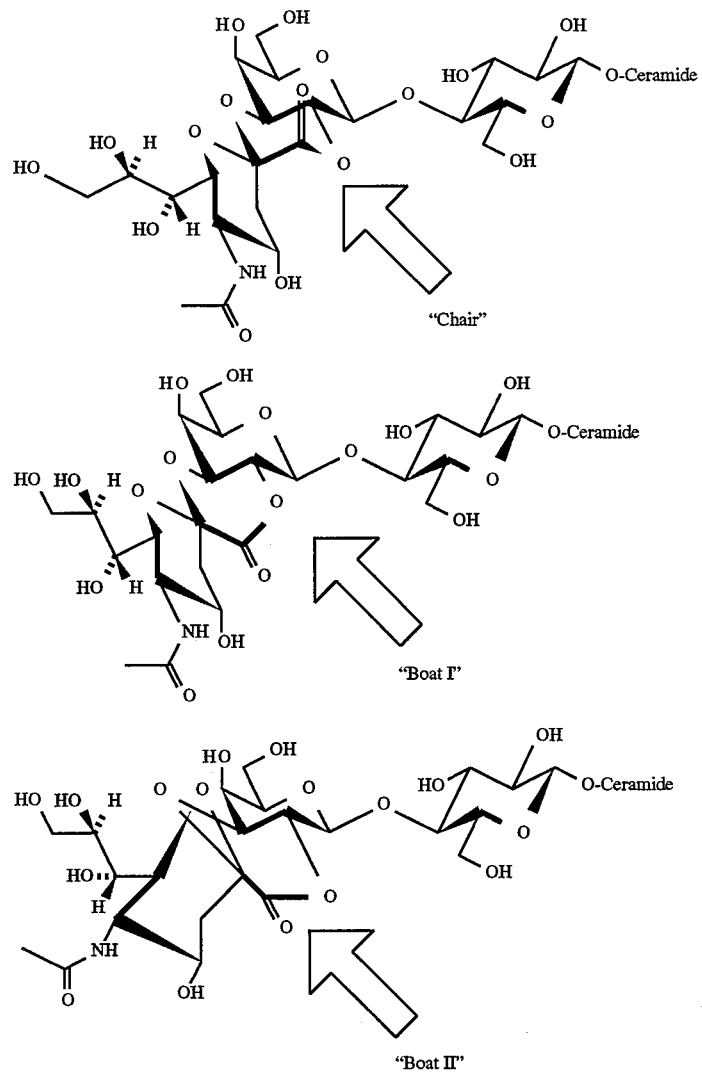

SCHEME 1

"Chair"

"Boat I"

"Boat II"

The evidence for boat-like conformations of the lactone ring rests on two observations:

i) the NMR signal of H-4 in the sialic acid residue of the GM₃-lactone is shifted downfield by ~0.6 ppm as compared to the parent GM₃-ganglioside. Such strong deshielding effects are indicative of a close contact in space (H . . . O-distance <2.7 Å) between the hydrogen atom in question and an oxygen atom (Bock, K; Kihlberg, J.; Magnusson, G. *Carbohydr. Res.* 1988, 176, 253). In the two boat-like conformations (Scheme 1) the distance between H-4 of the sialic acid residue and the carbonyl oxygen is ~2.5 Å, whereas this distance is considerably longer (~3.0 Å) in the chair-like conformation;

ii) molecular mechanics calculations (see U. Burkert and N. L. Allinger *Molecular Mechanics*, Am. Chem. Soc. USA, 1982) with $GM_3$-lactone showed that a boat-like conformation is considerably more stable than a chair-like conformation. Thus, even when the latter was used as the starting conformation in the calculations, the boat-like conformation was obtained after energy minimization.

The molecular construction and energy minimization calculations were carried out on a Apple Macintosh personal computer using the MacMimic/MM2 (91) software package (from InStar Software, Ideon Research Park, S-22370 Lund, Sweden) with the dielectric constant set at 80.

Figure 2:
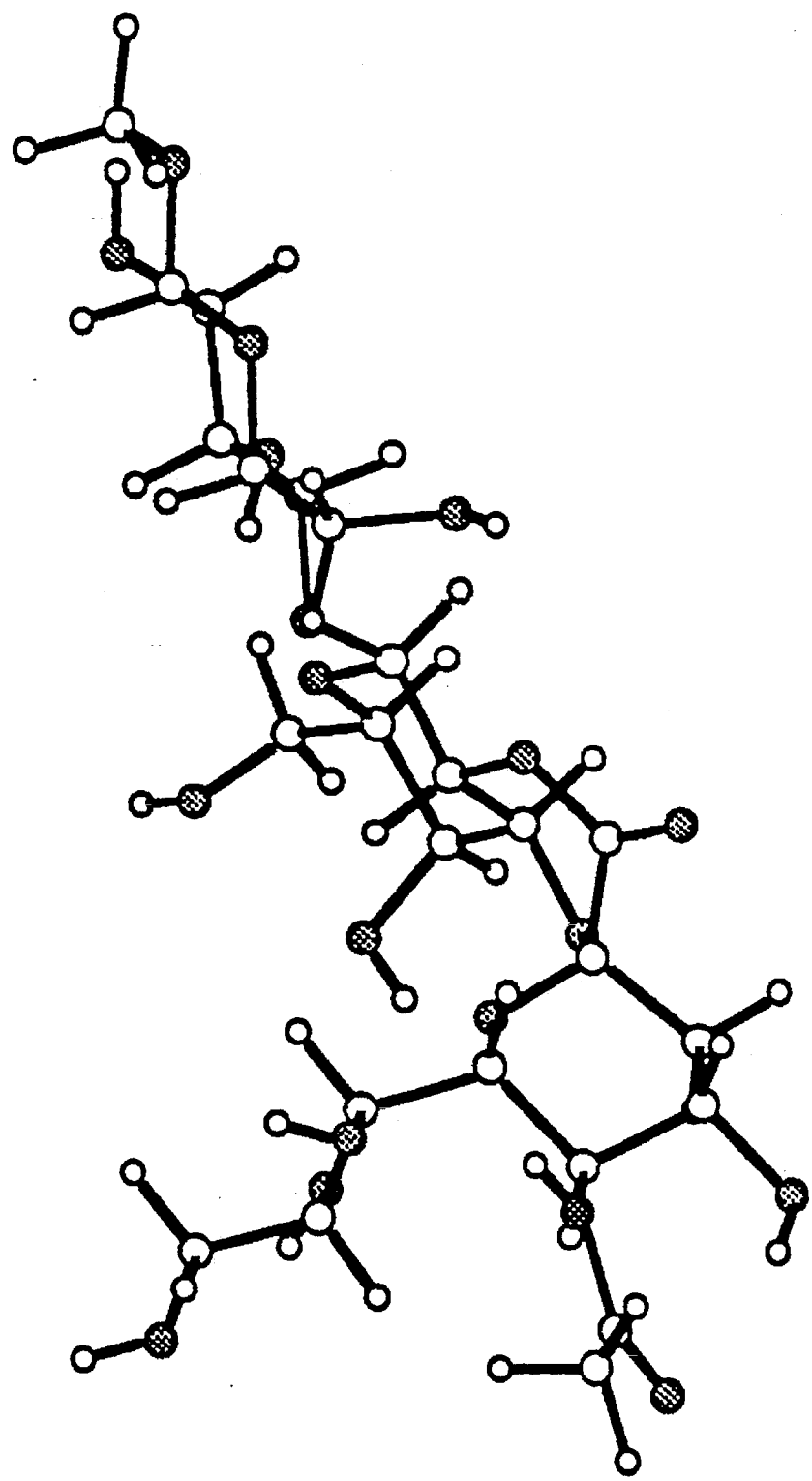
FIG. 2 shows a two-dimensional rendering of the energy-minimized three-dimensional structure of the methyl glycoside of the $GM_3$-lactam prepared in example 1.
Figure 3:
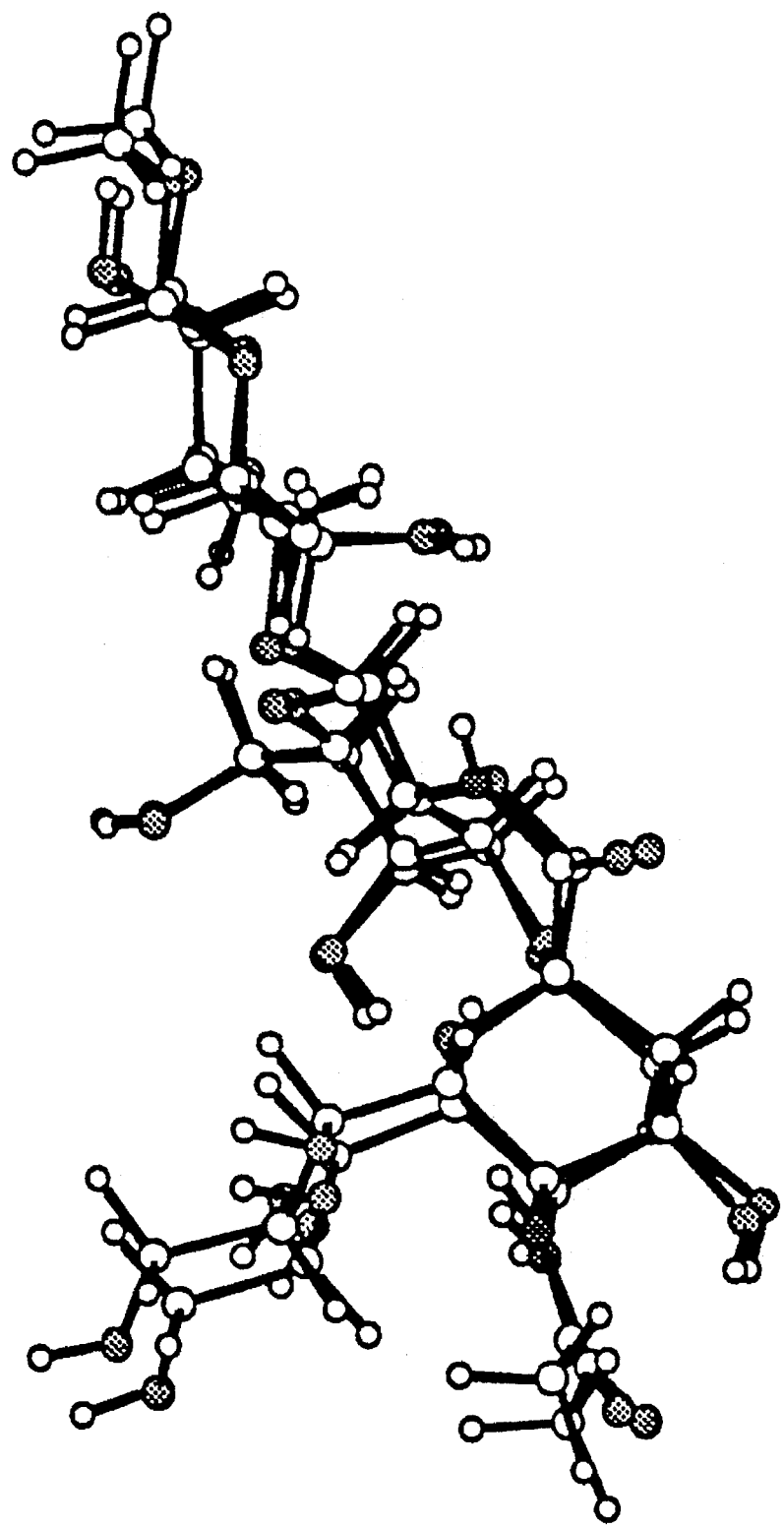
FIG. 3 shows a superimposition of the two structures shown in FIGS. 1 and 2.

Similar calculations for the corresponding lactam (the bovine serum albumin conjugate of which was prepared in Example 1 as compound 18) also resulted in the boat-like conformation. Furthermore, superimposition and RMS-fitting (by means of the above-described software) of the low-energy boat conformations of $GM_3$-lactone and $GM_3$-lactam using all the ring atoms of the corresponding methyl glycosides showed them to have very similar over-all shapes with the RMS error being as low as 0.097 Å. This relationship is depicted on the drawing where FIG. 1 shows the energy-minimized structure of $GM_3$-lactone methyl glycoside, and FIG. 2 shows the energy-minimized structure of $GM_3$-lactam methyl glycoside. FIG. 3 is a superimposition of FIGS. 1 and 2 and clearly illustrates the very close similarity in structure between on the one hand the natural but hydrolytically unstable ganglioside lactone and on the other hand the analogous synthetic and hydrolytically stable ganglioside lactam according to the invention which indicates that the two compounds are potentially able to exert the same biological activity. For example, $GM_3$-lactam, coupled to bovine serum albumin (Compound 18 in Example 1), should induce an immune response similar to that of the $GM_3$-lactone antigen (see Nores et al. cited above), and antibodies should cross-react with the respective antigens. These lactams should be stable against hydrolytic cleavage in vivo and therefore keep up a high concentration of antigen.

Example 5

Immunization Studies
Materials and Methods
Establishment of Monoclonal Antibodies.

The method of Köhler was followed (Immunol. Meth. II (1981), 285–298). The $GM_3$-lactam-BSA conjugate (18, 50 µg) was dissolved in phosphate-buffered saline (PBS, pH 7.2, 500 µl ), mixed with 500 µl of Freund's complete adjuvant (FCA, Sigma Chemical Co., St. Louis, Mo., USA) and injected subcutaneously (s.c.) into a Balb/c mouse. The immunization, now using the antigen with Freunds incomplete adjuvant (FIA), was repeated three times (s.c.) with one week intervals. After 20 days, the mouse received a final intravenous (i.v.) booster dose (50 µg of 18 in 100 µl of PBS) and seven days later it was splenectomized. The spleen cells were fused with Sp2/0 myeloma cells at the ratio 1:4 and hybridomas were screened for reactivity with coated $GM_3$-lactam-BSA (18, 3 µg/ml) in ELISA (see below).

A synthetic glucose-derived BSA conjugate (40, prepared from glucose pentaacetate in a manner analogous with the preparation of 18 above), corresponding to the inner part of 18, and BSA were used as negative controls. Cells from positive wells were expanded and recloned. More than 300 monoclonal hybridomas were established. Eight of the hybridomas were chosen at random and their specificities were investigated.

Tissue Culture.

Hybridoma cell lines were maintained in RPMI 1640 medium supplemented with 5% fetal calf serum, 100IU/ml penicillin and 1:50 dilution of hypoxanthin-thymidine (H.T.) supplement. All tissue culture media and supplements were from Gibco Ltd., Paisley, Scotland.

Specificity Testing by Binding to Neoglycoproteins and Glycolipids (Table 1).

$GM_3$-lactam-BSA (18), Glc-BSA (40), BSA, $GM_3$-ganglioside (41; obtained from Biocarb, Lund, Sweden) and $GM_3$-ganglioside lactone (42) (Yu, R. K., Koerner, T. A. W., Ando, S., Yohe, H. C. and Prestegaard, J. H. (1985) *J. Biochem.* 98, 1367–1373) were coated on microtiter plates using the method described by Nores et al. (*J. Immunol.* 139 (1987), 3171–3176). All compounds were used at concentrations of 3 µg/ml. Antibodies (100 µl of supernatant) were added to each of the coated wells and the amount of bound antibody was detected in ELISA as described below.

ELISA Screening.

ELISAs were performed by first binding the neoglycoproteins 18 and 40, and BSA (3 µg/ml in $NaHCO_3$-buffer, pH 9.6, 100 Ml ), and the gangliosides 41 and 42 (6 µg/ml in $CH_3OH$, 50 µl) to ELISA microplates (Costar, Cambridge, Mass, USA). The plates were left over night at 21° C. in a humified atmosphere (neoglycoprotein plates), or in a ventilated hood (gangliosides) and blocked with a BSA solution (1% in PBS buffer, 200 µl/well) for 30 min. The plates were washed with 3×200 µl of washing buffer (PBS-0.05% Tween 20). Hybridoma supernatant (100 µl) was added to each well, the plates were incubated for 2 h at 21° C., and washed with 3×200 µl of washing buffer. Rabbit antimouse-Ig/alkaline phosphatase-conjugate (Dako A/S, Glostrup, Denmark) in PBS containing 0.1% BSA was added to each well and the plates were incubated for 1 h at 21° C., and washed as above. The phosphatase substrate (p-nitrophenyl phosphate, 5 mg, tablet, Sigma Diagnostics, St. Louis, Mo., USA) was dissolved in 10 ml of substrate buffer (pH 9.8; 97 ml diethanolamine and 101 mg $MgCl_2 \cdot 6H_2O$, dissolved in $H_2O$ to a volume of 1000 ml) and added to the wells (200 µl/well). The plates were incubated for 30 min. at 37° C. and the optical density (OD) was measured at 405 nm with a Titertek Multiscan photometer (Flow Labs Ltd., Ayshire, Scotland). Sera from immunized and pre-immunized Balb/c mice were used as positive and negative controls, respectively.

Specificity Testing by Inhibition (FIG. 4).

The following 2-(trimethylsilyl)ethyl glycosides were used in the inhibition studies: $GM_3$-TMSEt (43), $GM_3$-lactam-TMSEt (12), $GM_2$-lactam-TMSEt (22) $GM_4$-lactam-TMSEt (29), $Gb_3$-TMSEt (44) (Kihlberg, J., Hultgren, S. J., Normrk, S. and Magnusson, G. (1989) *J. Am. Chem. Soc.* 111, 6364–6368), and asialo-$GM_2$-TMSEt (45) as well as asialo-$GM_1$-TMSEt (Ray, A. K. and Magnusson, G. (1992) *Acta Chem. Scand.* 46, 487–491).

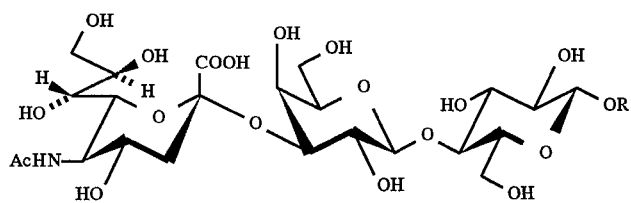
41 GM₃-Cer; R = Ceramide
43 GM₃—TMSEt; R = CH₂CH₂SiMe₃
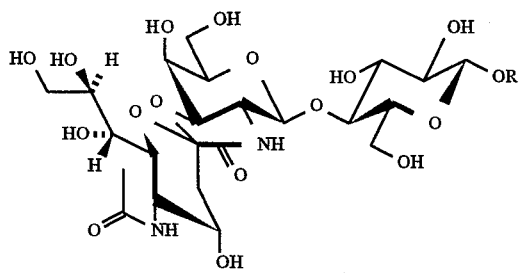
18 GM₃-lactam-BSA; R = CH₂CH₂SCH₂CH₂CONH—BSA
12 GM₃-lactam-TMSEt; R = CH₂CH₂SiMe₃
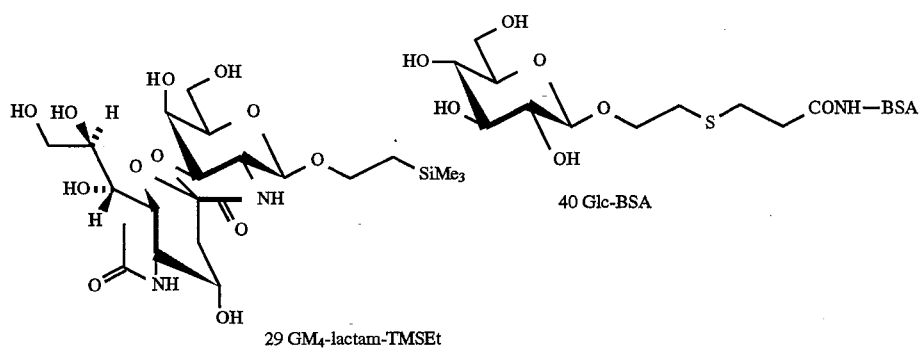
29 GM₄-lactam-TMSEt          40 Glc-BSA
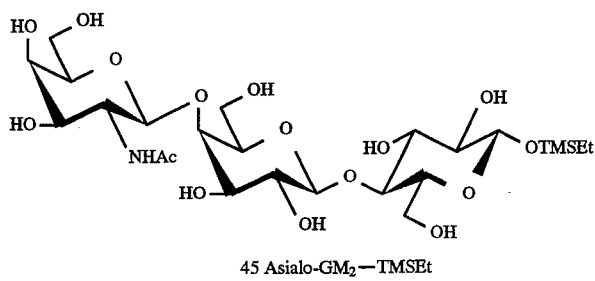
45 Asialo-GM₂—TMSEt
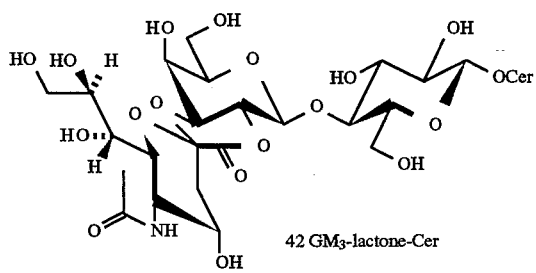
42 GM₃-lactone-Cer

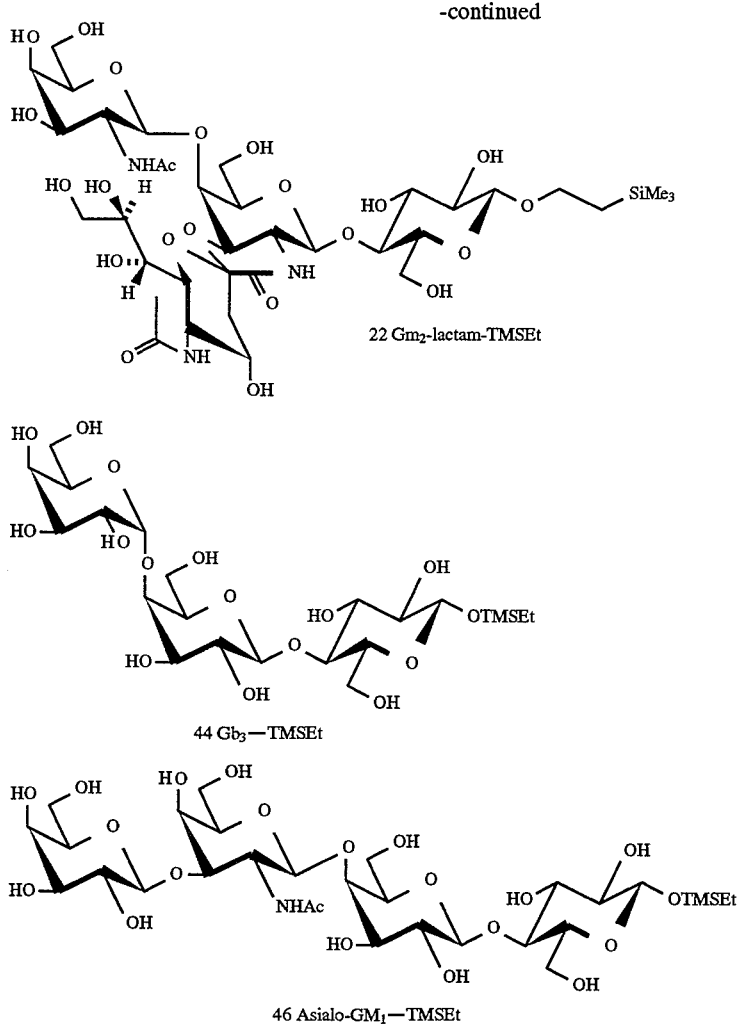

22 Gm₂-lactam-TMSEt

44 Gb₃—TMSEt

46 Asialo-GM₁—TMSEt

Each of the glycosides was dissolved in PBS buffer with 0.1% BSA to give a 2 mM solution, which was sequentially diluted with 5 volumes of PBS buffer in glass tubes. An aliquot (160 µL) of each saccharide solution was added to aliquots of the antibody solution (160 µl of supernatant), the plates were incubated over night at 4° C., and tested in ELISA (FIG. 4).

Isotyping of Monoclonal Antibodies.

Ig class and subclass testing of hybridomas was performed with a commercial dipstick kit (Holland biotechnology, Aj Leiden, The Netherlands).

Results and Discussion

By immunization of mice with GM$_3$-lactam-BSA (18), followed by establishment of hybridomas, a high number (>300) of antigen-specific clones were found. The majority of these clones recognized the sialyl-lactam-galactose portion of the antigen; clones recognizing the Glc-BSA structure (40) or BSA were not processed further. Considering the low immunogenicity of gangliosides in general, it is of special interest to note the high IgG response to GM$_3$-lactam, indicating its highly "non-self" structure and immunogenicity.

Eight randomly chosen hybridomas produced antibodies that were found to belong to the IgG, κ class (Table 1). They all recognized the antigen GM$_3$-lactam-BSA (18) coated on microtiter plates but did not bind to BSA, Glc-BSA (40), or GM$_3$-ganglioside lactone (42), thus meeting the objective to use a saccharide analog (18) for immunization and to obtain antibodies recognizing the natural counterpart (42).

TABLE 1

Binding specificity and subclass of eight randomly chosen monoclonal antibodies obtained by immunization with GM$_3$-lactam-BSA (18).

| Antibody | 18 | 42 | 41 | 40 | BSA | Subclass |
|---|---|---|---|---|---|---|
| P2-D10-H4-H9 (P2-1) | +++[a] | −[c] | − | − | − | IgG$_{2b}$, κ |
| P2-E12-C9-F9 (P2-2) | +++ | − | − | − | − | IgG$_{2b}$, κ |
| P3-A12-H4-F3 (P3) | +++ | − | − | − | − | IgG$_{2b}$, κ |
| P4-C7-H9 (P4-1) | +++ | − | − | − | − | IgG$_{2b}$, κ |
| P5-F12-D8-B2 (P5-1) | +++ | ++[b] | − | − | − | IgG$_1$, κ |
| P5-F12-E4-D4 (P5-2) | +++ | − | − | − | − | IgG$_1$, κ |
| P5-F12-G5-E6 (P5-3) | +++ | ++ | − | − | − | IgG$_1$, κ |

[a]+++, strong binding, ELISA optical density reading >1.5 at 405 nm.
[b]++, moderate binding, ELISA optical density reading ~1 at 405 nm.
[c]−, no binding.

The hybridomas P3, P5-1, and P5-3 were deposited on 25 June, 1992 in accordance with the provisions of The Budapest Treaty, with the European Collection of Animal Cell Cultures, Public Health Laboratory Service, Centre for Applied Microbiology and Research, Porton Down, United Kingdom, under the accession numbers 92062591, 92062592, and 92062593, respectively.

Figure 4A:
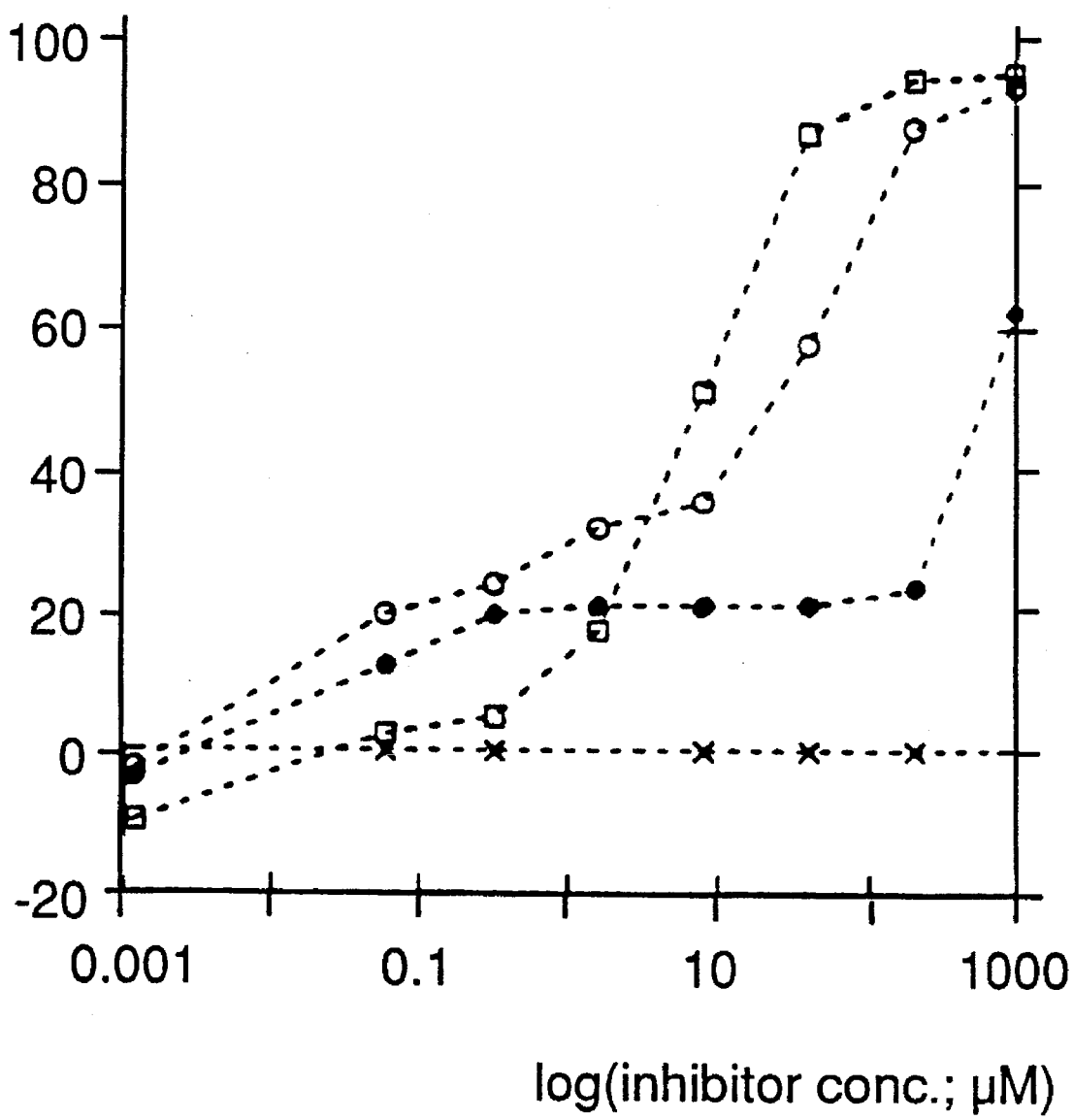
FIGS. 4 a–d shows inhibition curves for the binding of some monoclonal antibodies raised against $GM_3$-lactam-BSA conjugate, cf. Example 5 below.
Figure 4B:
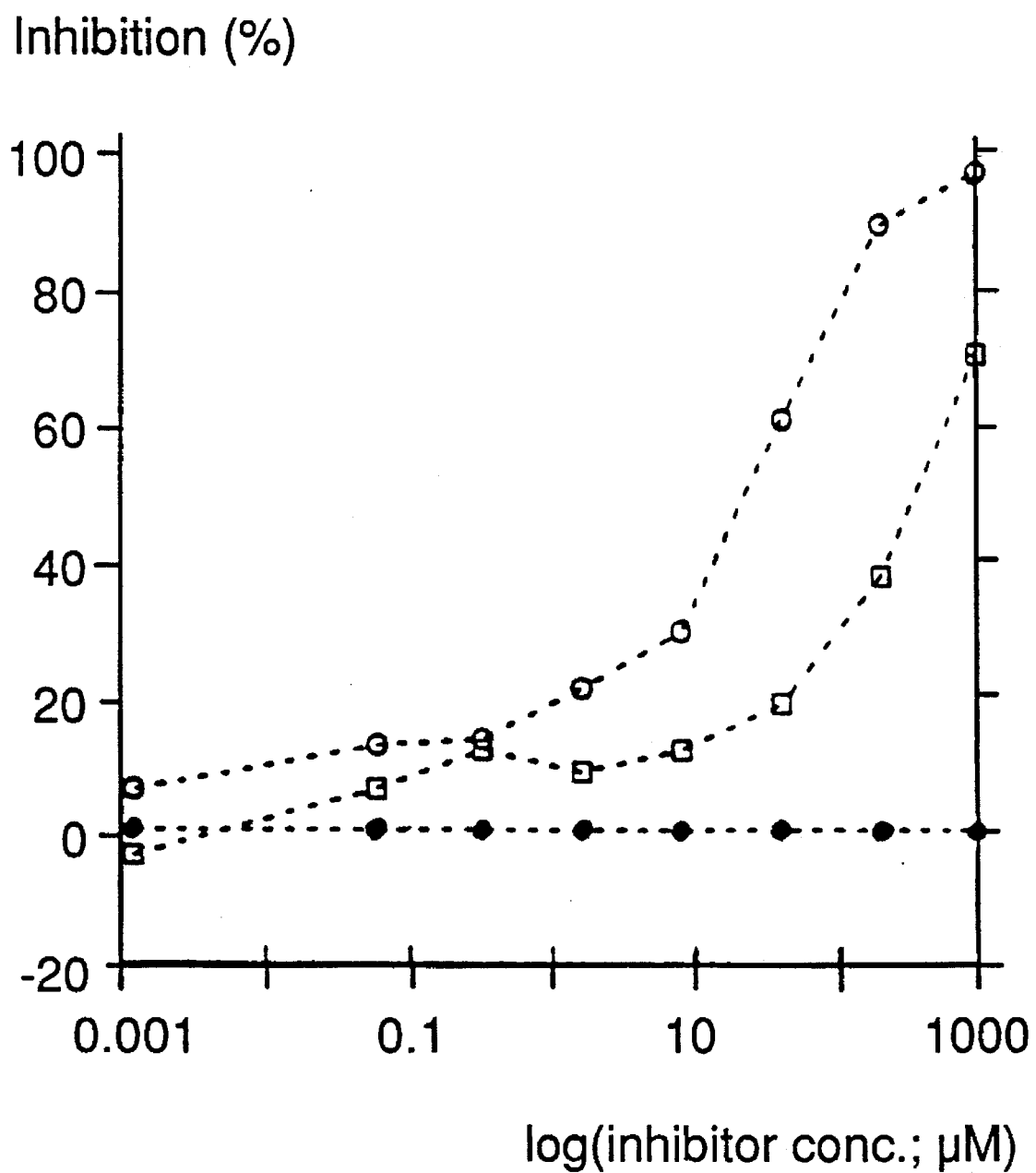
Figure 4C:
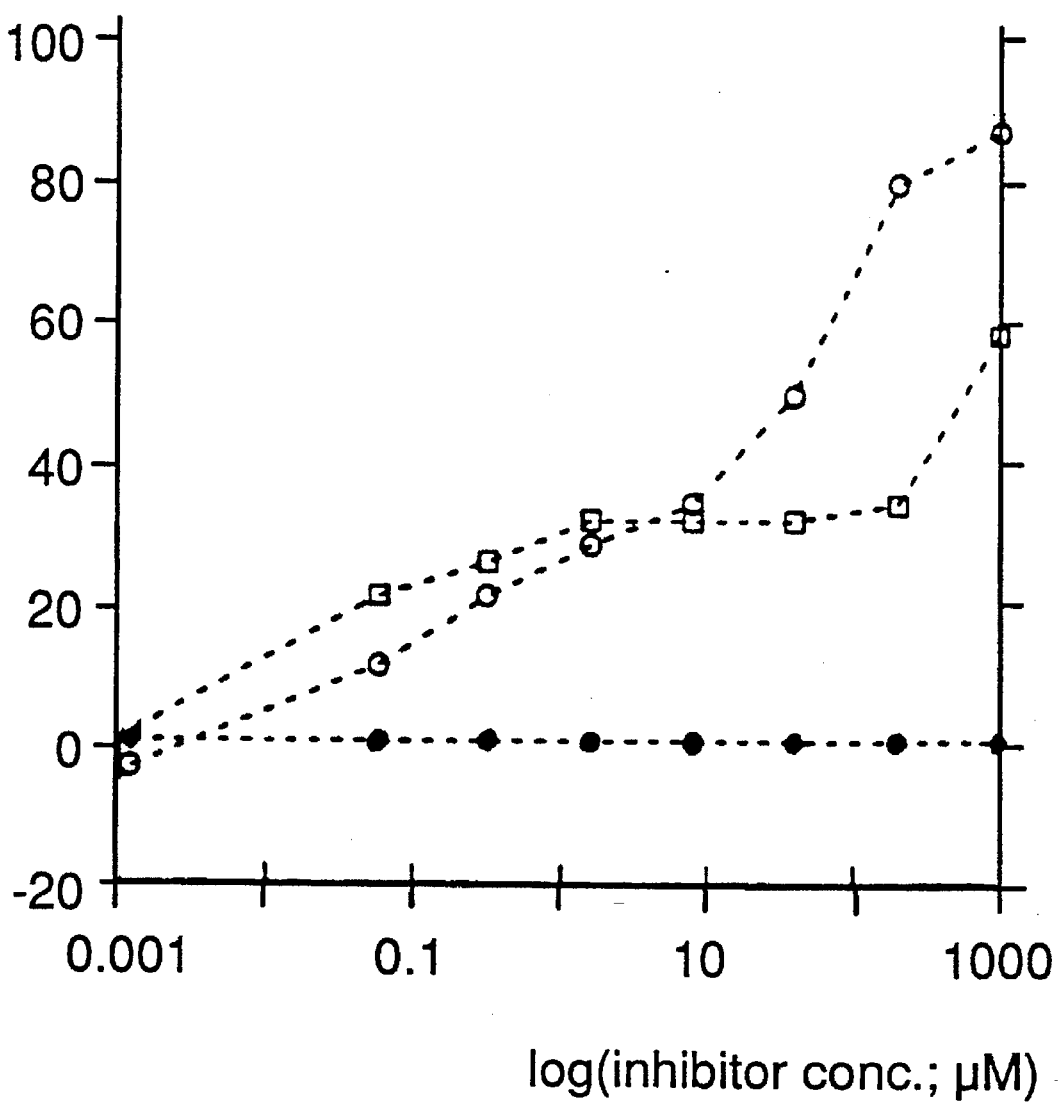
Figure 4D:
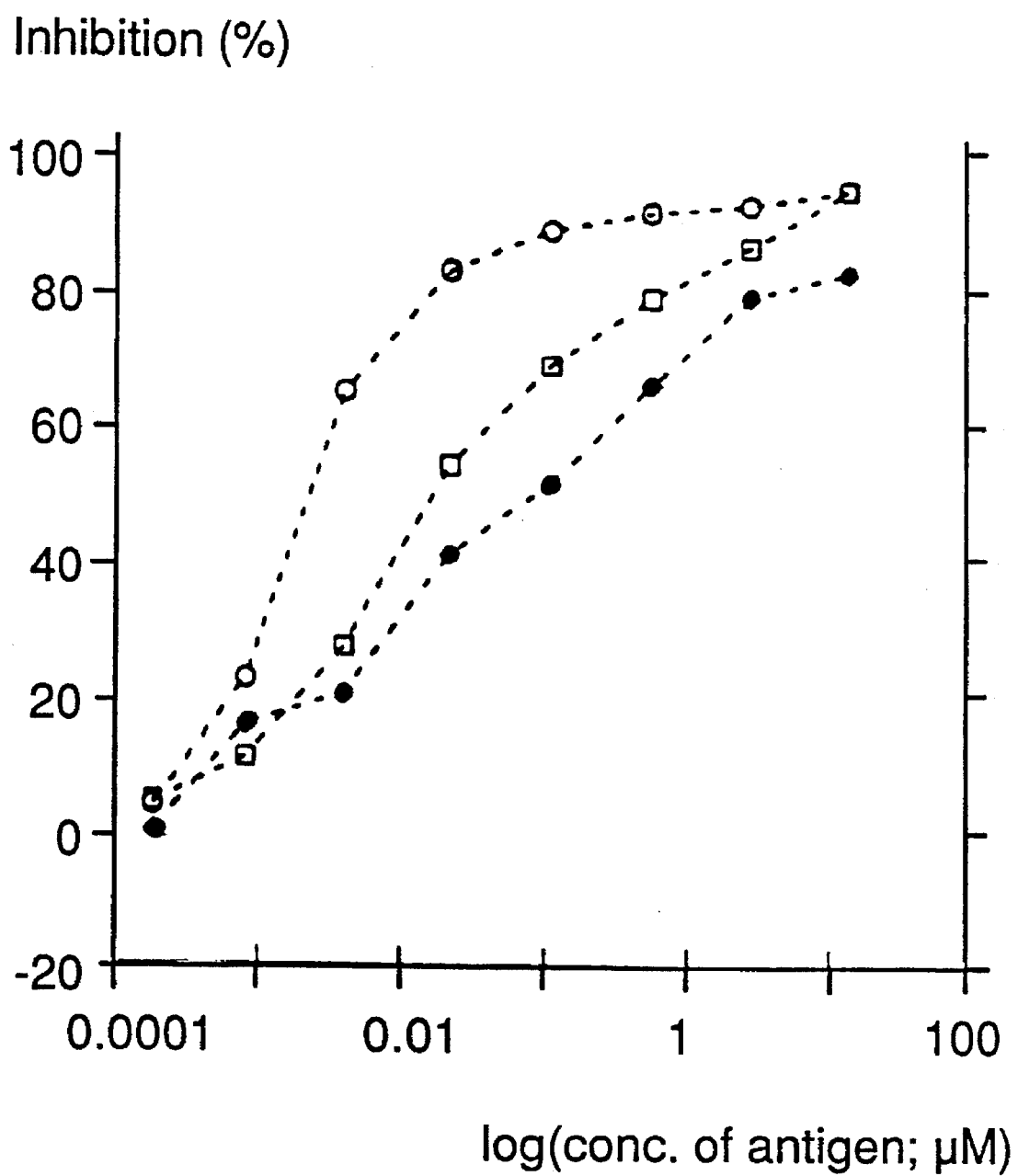

The ability of various compounds to inhibit the binding of the antibodies produced by the three deposited hybridomas identified above to the antigen (18) against which the antibodies were raised was tested as a function of concentration of inhibitor. FIG. 4A shows inhibition curves for antibody P3 as a function of the concentration of 12 (o), 22 (□), 29 (·) and 43, 44, 45, and 46 (x). FIG. 4B shows inhibition curves for antibody P5-1 as a function of the concentration of 12 (o), 29 (□), and 43, 22, 44, 45, and 46 (·). FIG. 4C. shows inhibition curves for antibody P5-3 as a function of the concentration of 12 (o), 29 (□), and 43, 22, 44, 45, and 46 (·). FIG. 4D shows the ability of the antigen in dissolved form to inhibit the binding of antibody P3 (o), P5-1 (□), and P5-3 (·) to the antigen immobilized on the test plates as a function of the concentration of the dissolved antigen.

As it will be seen from FIG. 4 a–d, the binding of antibody P5-1 and P5-3 to coated 18 was inhibited by soluble 18 and by the lactams 12 and 29, whereas the glycosides 43, 22 44, 45 and 46 were inefficient as inhibitors. The fact that $GM_2$-lactam-TMSEt (22) was inactive indicates that the antibody recognizes the epitope of lactamized (and lactonized) $GM_3$-saccharides which in the $GM_2$-lactam carries a sterically hindering GalNAc residue. Binding of antibody P3 (which did not recognize $GM_3$-ganglioside lactone 42) to coated 18 was inhibited by the lactams 12, 22, and 29. Obviously, the GalNAc residue of 22 did not hinder the binding. Thus, antibodies P3 and P5-1/P5-3 seem to recognize different saccharide epitopes. Since antibodies P5-1 and P5-3 recognize $GM_3$-ganglioside lactone (42) but not the open form of $GM_3$-ganglioside (41) (Table 1), they are potentially useful for selective immunohistological detection of $GM_3$-ganglioside lactone (42).

Of principal importance is the fact that these antibodies recognize both the natural $GM_3$-lactone as well as the synthetic $GM_3$-lactam, which further confirms that the saccharide conformations are very similar when bound by the antibodies. Therefore, stable ganglioside lactams may be generally useful substitutes for unstable ganglioside lactones in active immunization against ganglioside-expressing tumors and in other biomedical investigations.

We claim:

1. A compound which is a ganglioside lactam analogue derivative of the formula I

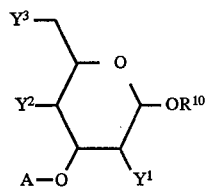

in which A is a sialic acid residue of the formula II

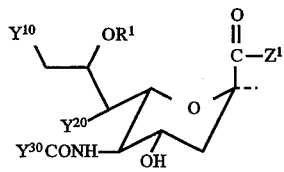

which is bound via the dashed line in the 2-position; and in which $Z^1$ is —OH or a group —$NHX^1$, and $Y^{30}$ is —$CH_3$ or —$CH^2OH$;

when $Z^1$ is —$NHX^1$, $X^1$ and $Y^1$ together form a bond and $Y^2$ is —OH or a group $OR^2$, or $X^1$ and $Y^2$ together form a bond and $Y^1$ is —OH or —NHAc;

$Y^3$ is —OH or a group —$OR^{20}$;

$R^1$ is H or a sialic acid residue of the formula III

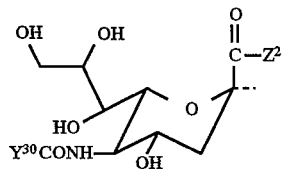

which is bound via the dashed line in the 2-position; and in which $Z^2$ is —OH or a group —$NHX^2$, and $Y^{30}$ is as defined above;

when $Z^2$ is —$NHX^2$, $X^2$ and $Y^{10}$ together form a bond and $Y^{20}$ is —OH, or $X^2$ and $Y^{20}$ together form a bond and $Y^{10}$ is —OH; with the provisos that when $R^1$ is H, then $Z^1$ is —$NHX^1$, and that when $R^1$ is a sialic acid residue of formula III above, then at least one of $Z^1$ and $Z^2$ is different from —OH;

$R^{10}$ is H, a carrier, or a group-$(Sugar)_n$, in which Sugar is a monosaccharide unit selected from the group consisting of D-glucose, D-galactose, D-mannose, D-xylose, D-ribose, D-arabinose, L-fucose, 2-acetamido-2-deoxy-D-glucose, 2-acetamido-2-deoxy-D-galactose, D-glucuronic acid, D-galacturonic acid, D-mannuronic acid, 2-deoxy-2-phthalimido-D-glucose, 2-deoxy-2-phthalimido-D-galactose, and sialic acid, and n is an integer from 1 to 10, and in which the reducing-end terminal sugar unit is either a hemiacetal or is glycosidically bound to a pharmaceutical or a carrier CA;

$R^{20}$ is a group of the formula I'

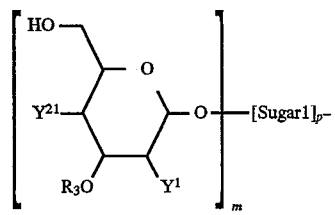

in which m is an integer 0 or 1; p is an integer from 1 to 5; Sugar1 is a monosaccharide unit selected from the group consisting of D-glucose, D-galactose, D-mannose, D-xylose, D-ribose, D-arabinose, L-fucose, 2-acetaraido-2-deoxy-D-glucose, 2-acetamido-2-deoxy-D-galactose, D-glucuronic acid, D-galacturonic acid, D-mannuronic acid, 2-deoxy-2-phthalimido-D-glucose, 2-deoxy-2-phthalimido-D-galactose, and sialic acid; and $R^3$ is H or a sialic acid residue of the formula II defined above, in which $Z^1$, $R^l$, $Y^{10}$, $Y^{20}$, $Y^{30}$ and $Z^2$ are as defined above, and $X^1$ and $Y^1$ together form a bond and $Y^{21}$ is —OH, or $X^1$ and $Y^{21}$ together form, a bond and $Y^1$ is —OH or —NHAc.

2. A compound as claimed in claim 1 in which at the most one of $Y^2$ and $Y^3$ is a group —$OR^{20}$.

3. A compound as claimed in claim 2 in which $Y^3$ is —OH and each Sugar unit in $R^{10}$, if present, as well as the ring structure and the Sugar1 unit in the formula I', if present, are selected from the group consisting of D-glucose, D-galactose, 2-acetamido-2-deoxy-D-galactose, and L-fucose units.

4. A compound as claimed in claim 3 in which the ring in the general formula I has the galacto configuration.

5. A compound as claimed in claim 4 in which $R^1$ is H.

6. A pharmaceutical composition for the treatment of human cancer having ganglioside lactones as cancer-associated antigens, which comprises a compound according to claim 1 and a pharmaceutically acceptable excipient.

7. The compound of claim 1 in which $R^{10}$ is a macromolecular carrier, or a group $-(\text{Sugar})_n$ in which the reducing-end terminal sugar is glycosidically bound to a macromolecular carrier.

* * * * *